(12) United States Patent
Saaski et al.

(10) Patent No.: US 8,012,229 B1
(45) Date of Patent: Sep. 6, 2011

(54) LIQUID PARTICULATE EXTRACTION DEVICE

(75) Inventors: Elric W. Saaski, Bothell, WA (US); Duane M. Fox, Snohomish, WA (US)

(73) Assignee: Research International, Inc., Monroe, WA (US)

( * ) Notice: Subject to any disclaimer, the term of this patent is extended or adjusted under 35 U.S.C. 154(b) by 0 days.

(21) Appl. No.: 12/925,978

(22) Filed: Nov. 3, 2010

Related U.S. Application Data

(62) Division of application No. 12/075,179, filed on Mar. 10, 2008, now Pat. No. 7,846,228.

(51) Int. Cl.
*B01D 46/18* (2006.01)

(52) U.S. Cl. ............ 55/406; 55/404; 55/405; 55/407; 55/400; 55/423; 95/270

(58) Field of Classification Search .......... 55/400, 55/404–407, 423; 95/270
See application file for complete search history.

(56) References Cited

U.S. PATENT DOCUMENTS

| | | | | |
|---|---|---|---|---|
| 2,195,707 A | * | 4/1940 | Nutting | 96/270 |
| 2,575,568 A | * | 11/1951 | Topanelian, Jr. | 96/217 |
| 3,005,515 A | * | 10/1961 | Caddell | 96/282 |
| 3,163,999 A | * | 1/1965 | Ditzler et al. | 62/469 |
| 3,448,858 A | | 6/1969 | Mills | |
| 3,751,886 A | * | 8/1973 | Sokolowski | 55/318 |
| 4,087,261 A | | 5/1978 | Hays | |
| 4,102,658 A | | 7/1978 | Jarvenpaa | |
| 4,238,210 A | | 12/1980 | Regehr et al. | |
| 4,437,867 A | * | 3/1984 | Lerner | 96/297 |
| 4,478,718 A | * | 10/1984 | Saget | 210/512.3 |
| 4,640,697 A | * | 2/1987 | Erickson, Jr. | 96/333 |
| 4,783,204 A | | 11/1988 | Roarty | |
| 4,850,537 A | | 7/1989 | Gourdine | |
| 4,922,691 A | * | 5/1990 | Shen | 55/400 |
| 4,938,785 A | | 7/1990 | MacPherson, Jr. et al. | |
| 5,755,096 A | * | 5/1998 | Holleyman | 60/407 |
| 5,814,216 A | | 9/1998 | Filion | |
| 5,885,333 A | | 3/1999 | Dix | |
| 6,484,594 B1 | | 11/2002 | Saaski et al. | |
| 6,532,835 B1 | | 3/2003 | Saaski et al. | |
| 6,672,387 B2 | * | 1/2004 | Brady et al. | 166/266 |
| 6,673,135 B2 | | 1/2004 | West | |

(Continued)

FOREIGN PATENT DOCUMENTS

DE 3345969 A1 7/1984

OTHER PUBLICATIONS

Entire U.S. Appl. No. 12/075,179, filed Mar. 10, 2008 for a Liquid Particulate Extration Device invented by Elric W. Saaski et al.

(Continued)

*Primary Examiner* — Jason M Greene
*Assistant Examiner* — Dung H Bui
(74) *Attorney, Agent, or Firm* — Gregory W. Moravan

(57) ABSTRACT

Extraction devices are disclosed for extracting liquid particulates from a gaseous stream. The extraction devices may have a powered or free spinning rotating extractor that may be mounted in the extraction device's source or extraction duct. During operation, liquid particulates impinging on the rotating extractor form a thin film of extracted liquid that travels due to centrifugal force to the periphery of the extractor's exterior surface where the extracted liquid may be flung to the inner surface of the extraction duct and collected.

23 Claims, 12 Drawing Sheets

U.S. PATENT DOCUMENTS

| | | | |
|---|---|---|---|
| 6,776,825 B2 | 8/2004 | Betting et al. | |
| 6,893,478 B2 * | 5/2005 | Care et al. | 55/337 |
| 7,001,448 B1 | 2/2006 | West | |
| 7,004,998 B2 | 2/2006 | Scherrer | |
| 7,022,153 B2 * | 4/2006 | McKenzie | 55/423 |
| 7,022,163 B2 * | 4/2006 | Olsson et al. | 95/268 |
| 7,156,901 B2 * | 1/2007 | Hallgren et al. | 95/270 |
| 7,159,533 B1 | 1/2007 | Redd et al. | |
| 7,241,392 B2 * | 7/2007 | Maier | 210/784 |
| 7,311,744 B2 * | 12/2007 | Elliott | 55/396 |
| 7,338,546 B2 * | 3/2008 | Eliasson et al. | 55/406 |
| 7,497,897 B2 * | 3/2009 | Currle et al. | 95/270 |
| 7,628,836 B2 * | 12/2009 | Barone et al. | 55/406 |
| 7,632,326 B2 * | 12/2009 | Stemmer | 55/400 |
| 7,662,220 B2 * | 2/2010 | Fukano et al. | 55/401 |
| 7,682,415 B2 * | 3/2010 | Mueller et al. | 55/434 |
| 7,749,310 B2 * | 7/2010 | Lagerstedt et al. | 95/270 |
| 7,833,303 B1 * | 11/2010 | Higgins | 55/400 |
| 2002/0139249 A1 * | 10/2002 | Livingston et al. | 95/270 |
| 2004/0159085 A1 * | 8/2004 | Carlsson et al. | 55/406 |
| 2004/0226442 A1 * | 11/2004 | Olsson et al. | 95/270 |
| 2005/0198932 A1 * | 9/2005 | Franzen et al. | 55/406 |
| 2005/0235617 A1 * | 10/2005 | Read | 55/423 |
| 2007/0240391 A1 | 10/2007 | Becker et al. | |
| 2009/0000258 A1 * | 1/2009 | Carlsson et al. | 55/400 |

OTHER PUBLICATIONS

USPTO Notice of Allowability, 7 pages, dated Aug. 11, 2010, regarding reference ABI.

* cited by examiner

Fig. 1: Prior Art

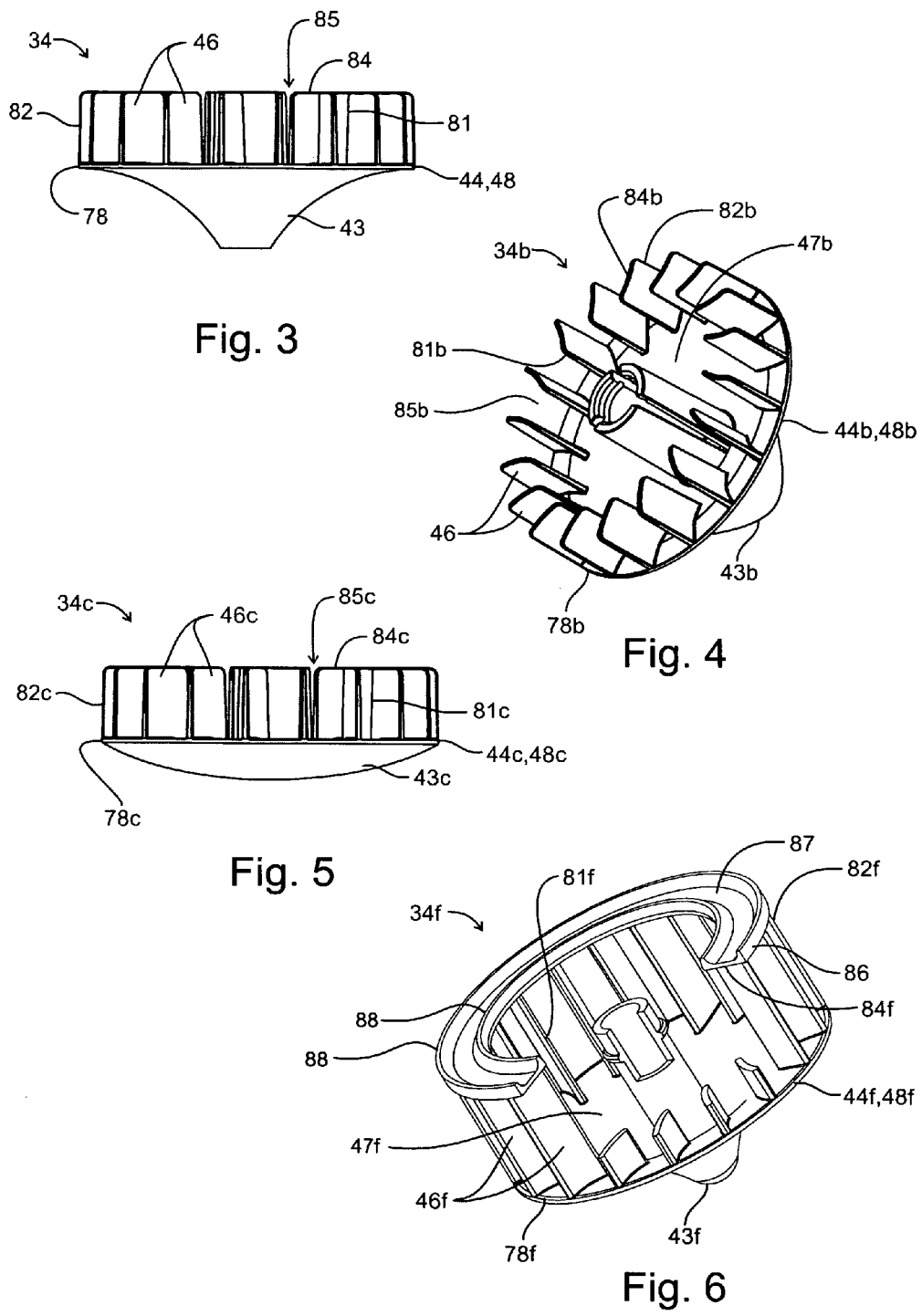

US 8,012,229 B1

LIQUID PARTICULATE EXTRACTION DEVICE

CROSS-REFERENCE TO RELATED APPLICATIONS

This is a divisional of U.S. application Ser. No. 12/075,179 filed on Mar. 10, 2008 now U.S. Pat. No. 7,846,228. Under 37 CFR 1.57, the forgoing parent application is hereby incorporated by reference in this divisional application.

STATEMENT REGARDING ANY FEDERALLY SPONSORED RESEARCH OR DEVELOPMENT

The invention was not made by an agency of the United States Government or under a contract with an agency of the United States Government.

BACKGROUND OF THE INVENTION

The present invention relates to devices for extracting particulates from a gaseous stream. More particularly, it relates to an extraction device for extracting liquid particulates from a gaseous stream.

BRIEF DESCRIPTION OF THE SEVERAL VIEWS OF THE DRAWING

FIG. 3 is a side elevational view of the extraction device's extractor;

FIG. 4 is a top perspective view of a first alternative form thereof;

FIG. 5 is a side elevational view of a second alternative form thereof;

FIG. 6 is a top perspective view of a third alternative form thereof;

DETAILED DESCRIPTION OF THE INVENTION

There are many applications that require the extraction of liquid particulates from a gaseous stream. For example, in steam turbines it is desirable to remove water particles from the steam driving the turbine, in order to minimize pitting and corrosion of the turbine's high-speed vanes.

As a further example, it is desirable to remove water particles from the air discharged from air humidifiers and devices that cool air by evaporation, such as those used in hospitals, office buildings, hotels and ships. It is desirable to remove such water particles because they may contain infectious agents such as bacteria or viruses, and may be particularly effective at lodging in respiratory tracts and transmitting disease.

Figure 1:
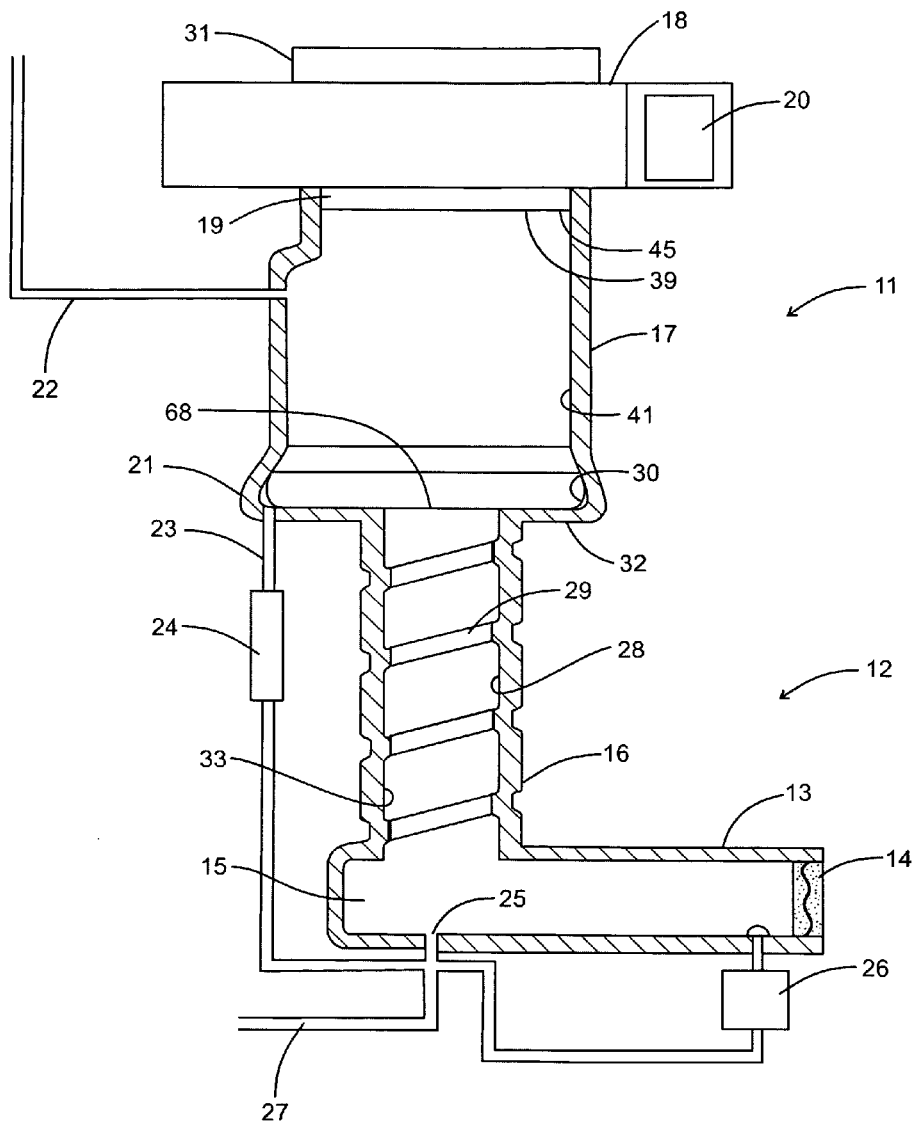
FIG. 1 is a side elevational view, partly in cross-section, of a prior art wetted surface air sampler.

Wetted surface air samplers are an example of a type of device that requires the extraction of liquid particulates from a gaseous stream, such as the air sampler 11 of FIG. 1, which is disclosed in U.S. Pat. No. 6,532,835. All of the disclosures of that patent are hereby incorporated by reference herein. In such air samplers, where the objective is to extract a target material from the sampled air and to place it in a small amount of stripping liquid within the air sampler 11, it is desirable to minimize loss of the stripping liquid caused by particles of the stripping liquid that are entrained in the discharged air. The target material may a liquid, solid, gas or vapor.

The liquid particulate extraction device 10 of the present invention may be designed to extract any desired entrained liquid particulates from any gaseous stream of interest. The liquid particulates may comprise any liquid, or any mixture of different liquids; and the liquid(s) may carry solid or dissolved materials. Similarly, the gaseous stream may comprise any gas or vapor, or any mixture of different gases or vapors; and the gas(es) or vapor(s) may carry particles of one or more different kinds of solid materials. The extraction device 10 may also be used to increase the extraction of solid particulates suspended in a gaseous stream, since in most cases the kinetics of airborne solid particles will be similar to those of liquid particulates.

The liquid particulate extraction device 10 may be adapted to be installed in, or used with, any piece of equipment having a gaseous stream containing entrained liquid particulates. Such equipment may be as simple as a pipe or duct containing the gaseous stream (e.g., a steam supply pipe for a turbine), or it may be more complex, such as the air sampler 11. Such equipment may receive the gaseous stream from an outside source, or the equipment itself may cause the gaseous stream to flow. The extraction device 10 may cause, or augment, the flow of the gaseous stream through the equipment. In view of all of the disclosures herein, a person of ordinary skill in the art would be able to easily make any modifications necessary to such equipment and the extraction device 10 so that the extraction device 10 could be installed in, or used with, any particular desired piece of equipment.

By way of example, the extraction device 10 will be described as being used with the air sampler 11 of FIG. 1, in which the stripping liquid is water, the liquid particulates are water particles, and the gaseous stream is air. The air sampler 11 may comprise a main body 12, an air inlet 13, an air filter 14, and a fan 18 for urging air through the air filter 14, air inlet 13 and main body 12.

Figure 2:
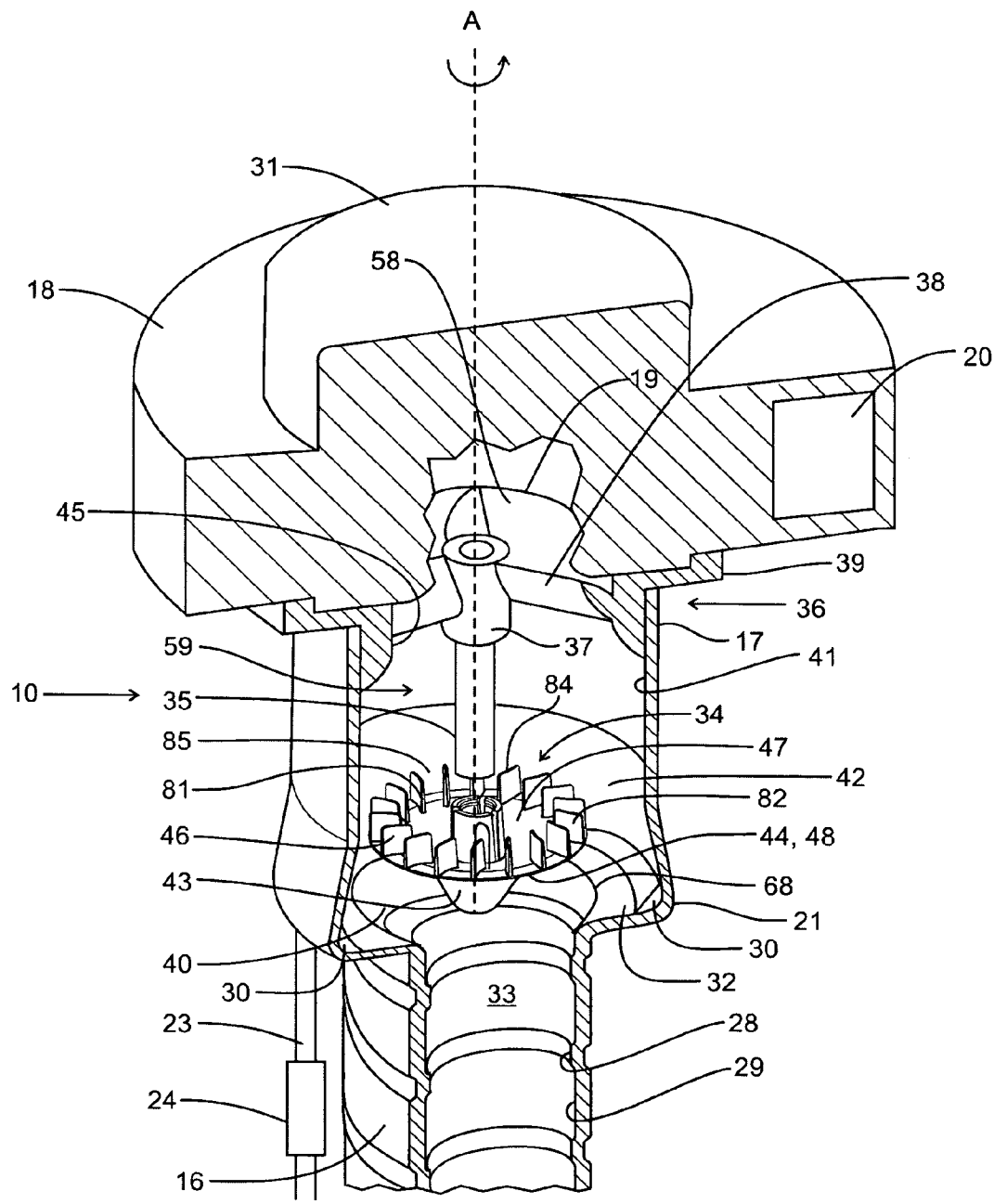
FIG. 2 is a side perspective view, partly in cross-section, of a first embodiment of the liquid particulate extraction device of the present invention shown installed in the air sampler of FIG. 1, with part of the air sampler being broken away.

The main body 12 may comprise a cyclonic cup 15, a source duct 16 (which may be called a stripping column), and an extraction duct 17 (which may be called a demister) having a larger cross-sectional area than that of the source duct 16. In addition to the other functions the source duct 16 may serve in the air sampler 11, it may also serve to supply the extraction duct 17 with a gaseous stream having entrained water particles. A connector 32 may connect the source and extraction ducts 16, 17. A reservoir 21 may be formed in any suitable way, such as by a radially enlarged lower portion of the extraction duct 17, as seen in FIGS. 1-2, or by an at least generally annular depression in the connector 32. The air sampler 11's air inlet 13 may enter the cyclonic cup 15 at a tangent, so that the incoming air may create an upwardly rising air vortex that effectively distributes the water within the cyclonic cup 15, source duct 16 and extraction duct 17 though impact and shear effects.

The fan 18 may have a fan motor 31, an air inlet 19 and an air outlet 20, with its air inlet 19 being connected to the extraction duct 17 in any suitable way, such as by being sized to fit over the air outlet 45 of the extraction duct 17. The water may be supplied to the air sampler 11 from a supply conduit 22 and may travel sequentially into the extraction duct 17, its reservoir 21, the reservoir 21's extracted water outlet (e.g., output conduit 23), through a water level control device 24 for the reservoir 21, into the cyclonic cup 15's liquid input port 25, and into the air inlet 13's fog generator 26, which generates a fog of water particles. Alternatively, water may be either supplied or removed from the air sampler 11 in any other suitable way, such as by using a T-style fitting attached to sample conduit 27. The cyclonic cup 15's liquid input port 25 may also be equipped with any suitable device for generating a fog of water particles.

The water level control device 24 may be connected to any suitable control device for the supply conduit 22, to regulate within any predetermined desired parameters the amount of water within the air sampler 11 (i.e., the air sampler 11's water inventory). Samples of the water may be withdrawn as needed from a sample conduit 27.

During operation of the air sampler 11, the sampled air (which may carry the target material of interest) may be sucked by the fan 18 through the air pre-filter 14 (which may be used to prevent the ingress of airborne debris), into the air inlet 13 where it will pass through a fog of water particles from the fog generator 26. As sampled air enters the cyclonic cup 15 it forms a rising, rapidly swirling air vortex that may aspirate an additional fog of water particles from the cyclonic cup 15's liquid input port 25. The fog of water particles within the air sampler 11 will strip at least some of the target material from the sampled air.

The centrifugal force generated by the rapidly swirling air vortex within the cyclonic cup 15 and source duct 16 may cause at least some of the fog of water particles (and any target material they carry), to move away from the center of rotation of the air vortex, and to then coalesce and form a thin film of extracted water on cyclonic cup 15's inner surface and source duct 16's inner surface 33. The rising air vortex may then cause that film of extracted water to climb up the inner surface 33, and to then cause that film of extracted water to spread radially outward across the connector 32 into the reservoir 21 and form a pool 30 of extracted water.

The source duct 16's inner surface 33 may be provided with a spiral, upwardly rising groove 28 defined by a spiral, upwardly rising boss 29, to aid in uniform distribution of the thin film of extracted water on the inner surface 33, and to further enable target material stripping from the air vortex.

As the rising, rapidly swirling air vortex from the source duct 16 enters the larger cross-sectional area extraction duct 17, its rotational and vertical velocities will decrease substantially. As a result, some of the larger diameter water particles (which may be formed by the spontaneous coalescing of some of the fog of water particles, or which may be formed from air-entrained extracted water from the source duct 16's inner surface 33), may no longer be supported by the slower moving air vortex within the extraction duct 17. As a result, some of the larger diameter water particles in the air vortex may fall directly onto the connector 32 between the source and extraction ducts 16, 17 and become extracted water. The air vortex will then urge that extracted water to travel radially outward into the pool 30 in reservoir 21. The centrifugal force generated by the air vortex within the extraction duct 17 may cause smaller, diameter water particles in the air vortex to be deposited on the extraction duct 17's inner surface 41, to coalesce and form a thin liquid film of extracted water on the inner surface 41, which can then travel down the inner surface 41 into the pool 30 in reservoir 21.

From the reservoir 21 the extracted water (and any stripped target material that it may carry) may then be recycled in the air sampler 11 by passing through the output conduit 23, the water level control device 24, the cyclonic cup 15's liquid inlet port 25, and the air inlet 13's fog generator 26. Each time the extracted water recycles through the air sampler 11, the concentration of the stripped target material in the extracted water will increase. This may be very important since the concentration of the target material in the sampled air may be very low, and therefore hard to detect. A sample of the extracted water may be withdrawn through the sample conduit 27 any time a test needs to be performed on the extracted water in the air sampler 11, such as to determine whether the target material is present, and if so, its amount or nature.

As has been mentioned, one purpose of the extraction device 10 of the present invention may be to effectively remove any entrained liquid particulates from any particular gaseous stream. For example, the extraction device 10 may be used to remove residual entrained water particles from the air stream it receives from the air sampler 11's source duct 16.

Turning now to FIG. 2, a first embodiment of the extraction device 10 is illustrated, by way of example, as being installed in the air sampler 11 of FIG. 1. The extraction device 10 may comprise a rotating extractor 34 and any suitable extractor mount that mounts the extractor 34 in any desired location in the source or extraction ducts 16, 17, such as the extractor mount 59. The extractor 34 has an exterior surface that may comprise an upstream surface 43, a side surface 48 and a downstream surface 47. The extractor mount 59 may comprise, for example, a mounting shaft 35 for the extractor 34, and a spider 36 for mounting the shaft 35 to the extraction duct 17's upper portion.

The extraction device 10 may further comprise part or all of the air sampler 11's source and extraction ducts 16, 17; and any suitable output device for removing from the source and extraction ducts 16, 17 the extracted water that has been extracted from the air stream by the extractor 34, such as the extracted water output conduit 23. Although only one conduit 23 is illustrated, there may be more than one conduit 23. Although the conduit 23's inlet is illustrated as being on the intersection 32 between the source and extraction ducts 16, 17, its inlet may be located in any suitable place within the source and extraction ducts 16, 17. Although the conduit 23 is illustrated as having only one inlet, it may have more than one inlet, each of which may be located in any suitable place within the source and extraction ducts 16, 17.

Any suitable source and extraction ducts 16, 17, besides those of the air sampler 11, may be used in conjunction with the extraction device 10, since the particular form of the source and extraction ducts 16, 17 used in conjunction with the extraction device 10 will depend on the particular piece of equipment having a gaseous stream with which the extraction device 10 is to be used.

Figure 9:
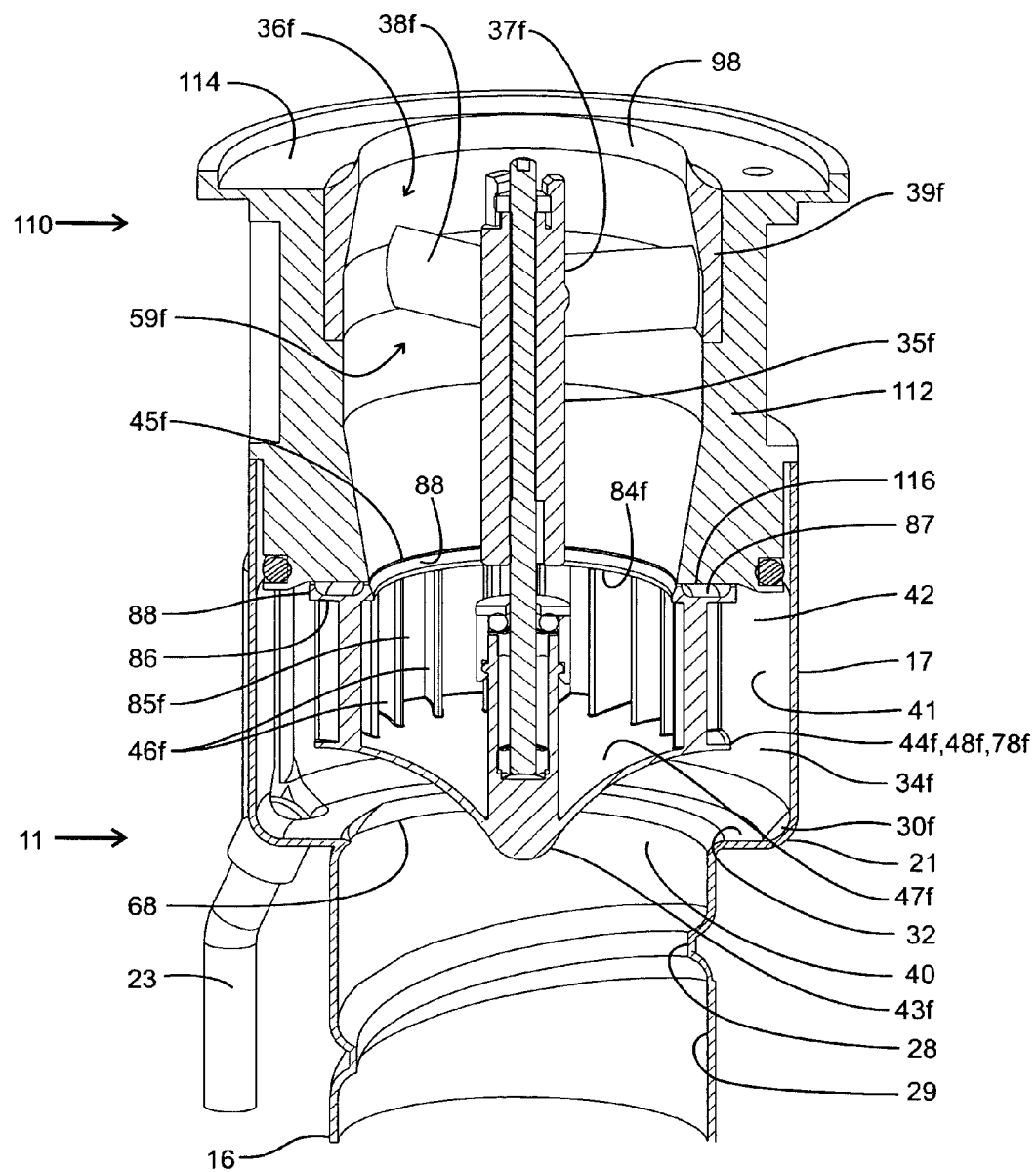
FIG. 9 is a perspective view, partly broken away, of a fourth embodiment of the liquid particulate extraction device of the present invention shown installed in the air sampler of FIG. 1.

Thus, the source and extraction ducts 16, 17 may have any suitable respective lengths, cross-sectional areas, cross-sectional configurations, shapes and sizes; any of which may, or may not, be the same for both the source and the extraction ducts 16, 17. Their respective cross-sectional areas, cross-sectional configurations, shapes and sizes may, or may not vary along their respective lengths, and may, or may not, be the same for both the source and the extraction ducts 16, 17. Although the source and the extraction ducts 16, 17 are illustrated in FIGS. 1, 2 and 9 as having at least generally circular cross-sectional configurations, their respective cross-sectional configurations may have any suitable geometric or non-geometric shape.

In addition, there may, or may not, be separate source and extraction ducts 16, 17 since the extraction duct 17 may serve one, more than one, or all of the functions of the source duct 16, and since the source duct 16 may serve one, more than one, or all of the functions of the extraction duct 17. Accordingly, when it is said, for example, that the gaseous stream passes though the extraction duct 17, or that the extractor 34 is mounted wholly or partly in the extraction duct 17, it is understood that such terminology covers the possibility that the source duct 16 is acting, in whole or in part, as an extraction duct 17. Similarly, when it is said, for example, that the gaseous stream passes though the source duct 16, or that the extractor 34 is mounted wholly or partly in the source duct 16, it is understood that such terminology covers the possibility that the extraction duct 17 is acting, in whole or in part, as a source duct 16.

The extraction device 10's spider 36 may comprise a hub 37, one or more arms 38, a peripheral adapter 39, and air channels 58 between the arms 38 through which the gaseous stream may exit the extraction device 10 and enter the fan 18's inlet 19. Two or three arms 38 may be preferred for physical stability, but a large number of arms 38 may result in undesirable excessive frictional losses between the arms 38 and the gaseous stream. The adapter 39 may have any suitable size, shape and construction, such as that illustrated in FIG. 2, and may serve to mount the arms 38 and the fan 18 to the extraction duct 17's top portion in any suitable way, such as with a friction fit between the adapter 39 and the duct 17's top portion, and a friction fit between the adapter 39 and a corresponding lower portion of the fan 18.

Any suitable power source may be used to cause the extractor 34 to rotate during use. For example, the power source may be the flow of the gaseous stream in the equipment (e.g., the air sampler 11) with which the extraction device is used, in which case the extractor 34 may be called a free spinning extractor 34, i.e., an extractor 34 that is caused to rotate, directly or indirectly, by the flow of the gaseous stream in the equipment with which it is used. Alternatively, the power source may be any suitable motor or other drive device for directly or indirectly causing the extractor 34 to rotate, in which case the extractor 34 may be called a powered extractor 34.

A free spinning extractor 34 may be provided in any suitable way. For example, the extractor 34 may be mounted on its mounting shaft 35 with any suitable bearing or bearing surfaces that permits it to rotate with respect to its mounting shaft 35, and any suitable number, type and size of vanes 46 may be mounted on its downstream surface 47 in any suitable locations. The gaseous stream passing by the extractor 34 drives the vanes 46, and causes the extractor 34 to rotate. A vane 46 is broadly defined to include any blade or other member that is suitable for imparting a rotational force to the extractor 34 when a gaseous stream acts on the blade or other member. Each vane 46 may have a radially innermost edge 81, a radially outermost edge 82, and a downstream edge 84; and there may be a channel 85 between each pair of adjacent vanes 46.

For certain types of wetted surface air samplers, such as the air sampler 11, it has been discovered that when the extractor 34 is designed to rotate at or near the rpm of the vortex formed by the gaseous stream within the source duct 16, sensitive target organisms in the liquid particulates entrained in the gaseous stream may be captured by the extractor 34's upstream surface 43 without as much risk of being harmed by impacting with excessive force on the upstream surface 43. This may be due to the matched, or nearly matched, rotational velocities of the upstream surface 43 and the liquid particulates entrained in the vortex formed by the gaseous stream within the source duct 16. Such undesirable excessive impact forces may occur in turbine-style wetted surface air samplers of the type described in U.S. Pat. No. 6,532,835, where the rotational velocities of the liquid particulates and the turbine are not matched, or nearly matched.

However, the extractor 34 may be designed to rotate at an rpm that is higher or lower than that of the vortex. The extractor 34 may be designed to rotate at any desired rpm in any suitable way, such as by suitably selecting the number, shape, size and location of the vanes 46, and by taking into consideration the composition, the longitudinal velocity, and the rotational velocity of the gaseous stream interacting with the vanes 46.

Alternatively, or in addition, any suitable number, type and size of vanes 46 may be placed on extractor 34's upstream surface 43 or side surface 48. However, vanes 46 on the upstream or side surfaces 43, 48 will reduce the smoothness and cleanability of those surfaces, and liquid may be trapped as liquid fillets at the intersections of the vanes 46 with the upstream or side surfaces 43, 48.

This means that vanes 46 on the upstream or side surfaces 43, 48 may be less desirable for use in wetted surface air samplers, such as the air sampler 11, where it may be desirable that the upstream and side surfaces 43, 48 be easily cleaned, and that as little as possible of the liquid in the air sampler 11 be trapped in surface pores or as liquid fillets on those surfaces, in order to make more of the liquid in the air sampler 11 available for recycling so that it may extract more target material from the gaseous stream, and in order to make more of the liquid in the air sampler 11 available to be removed through the sample conduit 27 for analysis.

If the vanes 46 and their associated mounting surfaces 43, 47 or 48 are made so that they effectively spin off the contents of any surface liquid films resident on them onto the extraction duct 17's inner surface 41, such as by making the vanes 46 and those mounting surfaces mirror-smooth and with generously radiused intersections between the vanes 46 and those mounting surfaces, then target material collection from the gaseous stream may be improved without a corresponding undesirable increase in trapped liquid on the vanes 46 and those mounting surfaces.

On the other hand, when the extraction device 10 is used with other kinds of equipment, such as with steam turbines or heat transfer systems, liquid trapping caused by surface roughness of the vanes 46 and their associated mounting surfaces 43, 47 or 48 or by the intersections between the vanes 46 and those mounting surfaces may be relatively unimportant, since such equipment may not have the same liquid handling constraints as the air sampler 11. However, having the extractor 34 rotate at or near the rpm of any vortex formed by the gaseous stream in that equipment may also be of benefit if impact pitting of the extractor 34's upstream surface 43 by the liquid particulates in the gaseous stream is of concern, since matching the rotational velocity of the extractor 34's upstream surface 43 with the rotational velocity of the gaseous stream in the equipment may reduce the force with which the entrained liquid particulates impact on the upstream surface 43.

As an alternative to having a fixed mounting shaft 35 on which the extractor 34 rotates, a free spinning extractor 34 may be created in any other suitable way, such as by fixing the extractor 34 to its mounting shaft 35 in any suitable way, and then mounting the mounting shaft 35 for rotation in the spider 36's hub 37 in any suitable way, such as by the use of a bearing or bearing surfaces, so that the extractor 34 and its mounting shaft 35 may freely spin as a unit when the vanes 46 are acted on by the gaseous stream. With such a construction, any suitable number, size and type of vanes 46 may be placed in any suitable locations on the shaft 35 in addition to, or in lieu of, the vanes 46 carried by the extractor 34.

As a further alternative, a free spinning extractor 34 may be created by fixing the extractor 34 to its mounting shaft 35 in any suitable way, fixing its mounting shaft to the spider 36's hub 27 in any suitable way, and mounting the spider 36's arms 38 for rotation with respect to the adapter 39 in any suitable way, such as by the use of a bearing or bearing surfaces, so that the extractor 34, mounting shaft 35, hub 27 and arms 38 may freely spin as a unit when the vanes 46 are acted on by the gaseous stream. With such a construction, any suitable number, size and type of vanes 46 may be placed in any suitable location on the shaft 35 and extractor 34.

As another alternative, or in addition, the arms 38 may take the form of vanes 46, which when acted on by the gaseous stream, may cause the extractor 34, mounting shaft 35, hub 27 and arms 38 to rotate. Having the arms 38 in the form of vanes 46 may offer the further advantage of such arms 38 using the undesirable but inevitable pressure drop that they create within the extraction duct 17 for causing rotation of the free spinning extractor 34.

A powered extractor 34 may be provided in any suitable way, such as by driving it, directly or indirectly, in any suitable way, with any suitable motor or other powered drive device, such as the fan motor 31. If the extractor 34 is driven directly by the fan motor 31, then it may be, for example, fixed in any suitable way to the fan motor 31's drive shaft 51 (e.g., see the extractor 34a of FIG. 11), in which case the extractor 34's mounting shaft 35 and spider 36 may be eliminated. On the other hand, if the extractor 34 is driven indirectly by the fan motor 31, this may be done in any suitable way, such as by fixing the extractor 34 in any suitable way to the fan rotor 52, such as by the use of at least one mounting arm 38a that extends between the extractor 34 and the adapter 39a or the fan rotor 52, in which case the extractor 34's mounting shaft 35 and spider 36 may again be eliminated.

Alternatively, a powered extractor 34 may be provided by fixing the extractor 34's mounting shaft 35 in place in the spider 36 in any suitable way, and then providing the extractor 34 with any suitable motor that drives it for rotation with respect to its fixed mounting shaft 35 in any suitable way.

Alternatively, a powered extractor 34 may be provided by transferring rotational force to the extractor 34 by using magnetic torque coupling, as is frequently used in packing-free liquid centrifugal pumps where a magnetic link is used to transfer rotational power through a hermetic diaphragm seal. Such an approach may eliminate corrosion of the drive motor 31's bearings that might otherwise be caused by the extracted liquid, and may minimize vibration transfer to extractor 34 that might otherwise be caused by the drive motor 31, thereby prolonging operating life of the extraction device 10.

Alternatively, a free spinning or powered extractor 34 may be mounted for rotation in any other suitable way within the source and extraction ducts 16, 17.

Optimum placement of the extractor 34 may be near the bottom of the extraction duct 17, immediately downstream from the source duct 16's outlet 68, as seen in FIG. 2, in order to permit the extractor 34 to intercept entrained liquid particulates that might otherwise be sucked into the fan 18.

Alternatively, as seen in FIG. 9, if duct 17's air outlet 45f is smaller than the average diameter of the duct 17, then it may be optimum to place the extractor 34f just upstream from the air outlet 45f so that the extractor 341's upstream surface 43f and rapidly rotating vanes 46f intercept entrained liquid particulates and prevent their egress through the air outlet 45f. The mounting sleeve 112 may be considered to be part of the duct 17 and may provide the duct 17's air outlet 45f and surface 116. However, it may be equally valid to consider that the mounting sleeve 112, its air outlet 45f, and its surface 116 may comprise part of the extractor mount 59f.

As an alternative to a separate mounting sleeve 112, an air outlet 45f and a surface 116 may be provided for the duct 17 in any other suitable way, such as by making the mounting sleeve 112 an integral part of the duct 17. The shape, form and construction of the mounting sleeve 112 (whether its integrally formed as part of the mounting sleeve or whether it is formed as a separate part) may be varied in any suitable way as long the duct 17 is provided with an air outlet 45f and a surface 116 that function in the manner described herein. As a further alternative, the air outlet 45f and surface 116 may be provided for the duct 17 by any other suitable structure besides the mounting sleeve 112.

In general, the extractor 34 will increase the overall frictional losses associated with the flow of the gaseous stream through the ducts 16, 17, independent of the axial location of the extractor 34 within the ducts 16, 17. Accordingly, it may be necessary to trade off the extractor 34's liquid particulate extraction efficiency against the frictional losses it causes to the flow of the gaseous stream. This may be conveniently done by adjusting the axial location of the extractor 34 in the ducts 16 or 17 and simultaneously recording the pressure drop it causes and the amount of liquid particulates it extracts from the gaseous stream.

Although the extraction device 10 is illustrated in FIG. 2 as being located at least substantially wholly within the extraction duct 17, it may be located partially in both the source and extraction ducts 16, 17, or it may be located at least substantially wholly within the source duct 16.

Although the extractor 34 and the source and extraction ducts 16, 17 are illustrated in FIG. 2 as being oriented so that they share a common vertical longitudinal axis A, they may be oriented so that their common axis A is horizontal, or at any angle between horizontal and vertical. In addition, the respective longitudinal axes A of the extractor 34 and the source and extraction ducts 16, 17 may not be coincident with each other.

As seen in FIG. 2, the cross sectional area of the extractor 34's upstream surface 43 may vary along its longitudinal axis A, and may have a maximum cross sectional area at the upstream surface 43's periphery 44. The upstream surface 43's maximum cross sectional area may be selected to be at least about equal to the inner cross-sectional area of the source duct 16's outlet 68 if the extractor 34 is located near the outlet 68; or at least about equal to the inner cross sectional area of the extraction duct 17's outlet 45 if the extractor 34 is located near the outlet 45. However, the upstream surface 43's maximum cross sectional area may be selected to be smaller or larger than the inner cross sectional areas of the duct 16's outlet 68 or the duct 17's outlet 45. As seen in FIG. 2, the extraction duct 17's outlet 45 may be defined, for example, by the spider 36's adapter 39.

For example, the upstream surface 43's maximum cross-sectional area may be selected to be in the range of from about 80% to 300% of the inner cross-sectional areas of the duct 16's outlet 68 or the duct 17's outlet 45. The selected maximum cross-sectional area of the upstream surface 43 may depend on a number of factors, including the size of the liquid particulates in the gaseous stream, the velocity of the gaseous stream as it passes through the source and extraction ducts 16, 17, the acceptable overall pressure drops caused by the extraction device 10 and its extractor 34, any changes in the extraction duct 17's inner cross sectional area along its axis A, and the upstream and downstream geometries of the source and extraction ducts 16, 17.

Whether the extractor 34 is located near the source duct 16's outlet 68 or near the extraction duct 17's outlet 45, most of the liquid particulates entrained in the gaseous stream will be extracted by the extractor 34, rather than escaping through the duct 17's outlet 45 along with the exiting gaseous stream. Either location of the extractor 34 increases the likelihood that any liquid particulates entrained in the gaseous stream from the source duct 16 will impact on the extractor 34's upstream surface 43, vanes 46, or both.

In general, for the reasons that will be made apparent by all of the disclosures herein, the effectiveness of the extractor 34's upstream surface 43 in extracting liquid particulates from a gaseous stream may be functions of: the extractor 34's axial location relative to the source duct 16's outlet 68 or extraction duct 17's outlet 45; the maximum cross sectional area of the upstream surface 43 as compared to the inner cross sectional area of the source duct 16's outlet 68 if the extractor 34 is located near to the outlet 68; the maximum cross sectional area of the upstream surface 43 as compared to the inner cross sectional area of the extraction duct 17's outlet 45 if the extractor 34 is located near to the outlet 45; and the rotations per minute (rpm) of its upstream surface 43, with its upstream surface 43 being, in general, increasingly more effective in extracting liquid particulates as its cross-sectional area and rpm are increased, and with it being, in general, increasingly less effective as its cross-sectional area and rpm are decreased. For example, as the cross-sectional area of its upstream surface 43 is increased, the probability of liquid particulates from a gaseous stream impacting on it is increased. By way of further example, in order to achieve a particular desired effectiveness at removing liquid particulates from a gaseous stream, a smaller cross-sectional area upstream surface 43 may have to be spun at higher rpm than would a larger cross-sectional area upstream surface 43. However, the upstream surface 43 may be at least partially effective even if its cross-sectional area is relatively small, and even if it is not rotating at all.

When the extractor 34 is mounted so that it is near the source duct 16's outlet 68 as seen in FIG. 2, the gaseous stream travels in a serpentine flow path around the extractor 34, executing a first 90° turn towards the periphery 44 of the extractor 34's upstream surface 43, then executing a second 90° turn to flow along the extractor 34's side surface 48, and then flowing radially inwardly behind the extractor 34's downstream surface 47. If the extractor 34 is located further away axially from the outlet 68, such as a distance equal to or greater than the upstream surface 43's maximum diameter, the gaseous flow path is qualitatively similar to that just described, but the amount of impingement of liquid particulates on its upstream surface 43 is reduced somewhat.

Independent of the axial placement of the extractor 34, it has been discovered that this serpentine flow path may be particularly effective at removing liquid particulates from the gaseous stream since a two-stage extraction process is created. In particular, in the first stage of the extraction process, the perpendicular component of the orientation of the extractor 34's upstream surface 43 relative to the flow of the gaseous stream creates a desirable geometry that may enhance the impingement of liquid particulates in the gaseous stream onto the upstream surface 43 as the gaseous stream executes its first 90° turn towards the upstream surface 43's periphery 44. This is because the momentum of the liquid particulates in the gaseous stream may desirably cause some of the liquid particulates to collide with the upstream surface 43, despite the gaseous stream executing its first 90° turn.

In the second stage of the extraction process, as the gaseous stream executes its second 90° turn to flow along the extractor 34's side surface 48 the momentum of the remaining liquid particulates in the gaseous stream may desirably cause some of the remaining liquid particulates to collide with the extraction duct 17's inner surface 41 despite the gaseous stream executing its second 90° turn.

It has also been discovered that the rotation of the extractor 34 during operation of the extraction device 10 may lead to the establishment of a desirable, unique swirling flow pattern in the gaseous stream from the source duct 16 as it encounters the rotating extractor 34, detours around it, and continues flowing downstream through the extraction duct 17. In general, the strength of the swirling flow pattern will be a complex function of many different factors, such as, for example, the extractor 34's rpm and the maximum cross sectional area of its upstream surface 43, the duct 17's inner cross sectional area, the axial location of extractor 34 between the duct 16's outlet 68 and the duct 17's outlet 45, and the longitudinal velocity of the gaseous stream as it passes through the duct 17.

It has been discovered that this swirling flow pattern in the gaseous stream may be advantageous since it may increase the residence time of the gaseous stream in the vicinity of the extractor 34's upstream surface 43 and in the vicinity of extraction duct 17's inner surface 41, thereby enhancing the probability that the liquid particulates in the gaseous stream will impact onto the upstream surface 43 and the inner surface 41, due to the centrifugal forces exerted by the swirling flow pattern on the liquid particulates. A non-rotating extractor 34 would not provide this advantage.

It has also been discovered that the rotating extractor 34 may also create a beneficial radial pumping of the gaseous stream that passes over its rotating upstream surface 43. This, in effect, creates a secondary centrifugal gas pump with a measurable and beneficial pumping effect on the gaseous stream that makes up in part for drag losses associated with the extractor 34 being located in the flowing gaseous stream. A non-rotating extractor 34 would not provide this advantage. However, if the extractor 34 is a free spinning extractor 34 then it may generally be desirable to mount its vanes 46 so they provide rotational torque to the extractor 34 from the flow of the gaseous stream around the extractor 34. The extractor 34 will then be extracting energy from the gaseous flow, and a balance between the extractor 34's droplet extraction effectiveness and energy consumption will have to be made.

It has been further discovered that a rotating extractor 34 may provide a desirable radial liquid pumping process for the film of extracted liquid on its upstream surface 43 and vanes 46. That is, liquid particulates from the gaseous stream that impinge on its upstream surface 43 and vanes 46 form a thin film of extracted liquid on its upstream surface 43 and vanes 46. Due to the centrifugal forces transferred to the film by the rotation of extractor 34, the film flows rapidly radially outward to the periphery 44 of the extractor 34's upstream surface 43, and to the outer edges 82 of the vanes 46, to form droplets of the extracted liquid that are then flung through the gaseous stream onto the extraction duct 17's inner surface 41. That extracted liquid may then be collected in any suitable way in the pool 30 in the reservoir 21, such as under the force of gravity, so that the extracted liquid may then be recycled, tested, or disposed of.

A non-rotating extractor 34 would not provide this advantage because the thin film of extracted liquid that formed on its upstream surface 43 and vanes 46 would only be subjected to shear forces associated with the gaseous stream flowing radially outward across its upstream surface 43, or flowing radially inward over its vanes 46.

Direct impingement of the gaseous stream onto its upstream surface 43 may be relatively ineffective at urging the thin liquid film of extracted liquid to flow across its upstream surface 43, depending on several factors such as, for example, the shape of its upstream surface 43 and the radial velocity of the gaseous stream flowing across its upstream surface 43. As a result, liquid particulates from the gaseous stream that impinged on its upstream surface 43 would tend to coalesce into a relatively thick film of extracted liquid that randomly dripped into the incoming gaseous stream from the source duct 16. Over time, if the gaseous stream also carried solid particulate material, its upstream surface 43 may become undesirably coated or caked with solid particulate material, since there is not the degree of flushing action that may be provided by a rotating extractor 34 that causes extracted liquid and other material on its upstream surface 43 to travel rapidly to its periphery 44.

In a similar manner, liquid particulates coalescing on the extractor 34's downstream surface 47 and vanes 46 to form a thin film of extracted liquid, would eventually randomly drip therefrom under the urging of the gaseous stream, may become entrained in the gaseous stream, and may undesirably exit with the gaseous stream through the extraction duct 17's outlet 45.

It has been discovered that a rotating extractor 34 also has several other advantages that are not so apparent. For example, it has been discovered that any films of extracted liquid created on its upstream surface 43 are very effective at capturing hydrophilic solid particulates suspended in the gaseous stream.

This may be of great importance in the design of certain devices, such as the wetted surface air sampler 11, which may have a limitation called "re-aerosolization". It is recalled that, by way of example, the extracted liquid in the air sampler 11 may be water; that the air sampler may be used for monitoring solid particulates, such as target pathogens, e.g., airborne spores, bacteria and viruses, which may be present in the gaseous stream (i.e., in the sampled air); and that the extracted water in such devices may be recirculated for long periods of time, to enhance the concentration in the extracted water of the target pathogen present in the sampled air as a very low concentration aerosol.

During the recirculation process, recirculated extracted water is sprayed into incoming sampled air to increase the concentration of the target pathogen in the extracted water. The recirculated extracted water may contain captured target pathogens, and some portion of the spray particles of the recirculated extracted water may evaporate as they are mixed with relatively dry incoming sample air, thereby releasing some of the previously captured target pathogens back into the sample air within the air sampler 11, leading to re-aerosolization losses of the previously captured target pathogens.

It has been discovered that the thin film of extracted water on the rotating extractor 34's upstream surface 43 is a very effective second-stage capture surface for such re-aerosolized target pathogens, and may reduce net loss rates of such re-aerosolized target pathogens by 3 times, or more, in wetted surface air samplers such as the air sampler 11.

Figure 7:
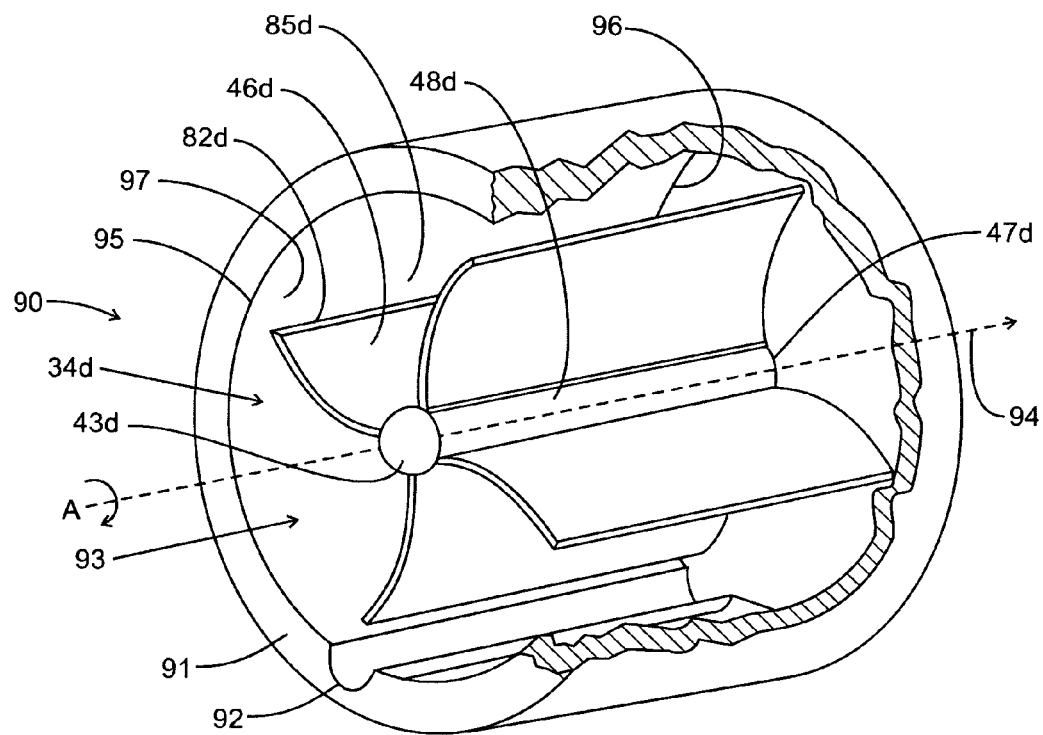
FIGS. 7 and 8 are perspective views, partly broken away, of second and third embodiments of the liquid particulate extraction device of the present invention.
Figure 8:
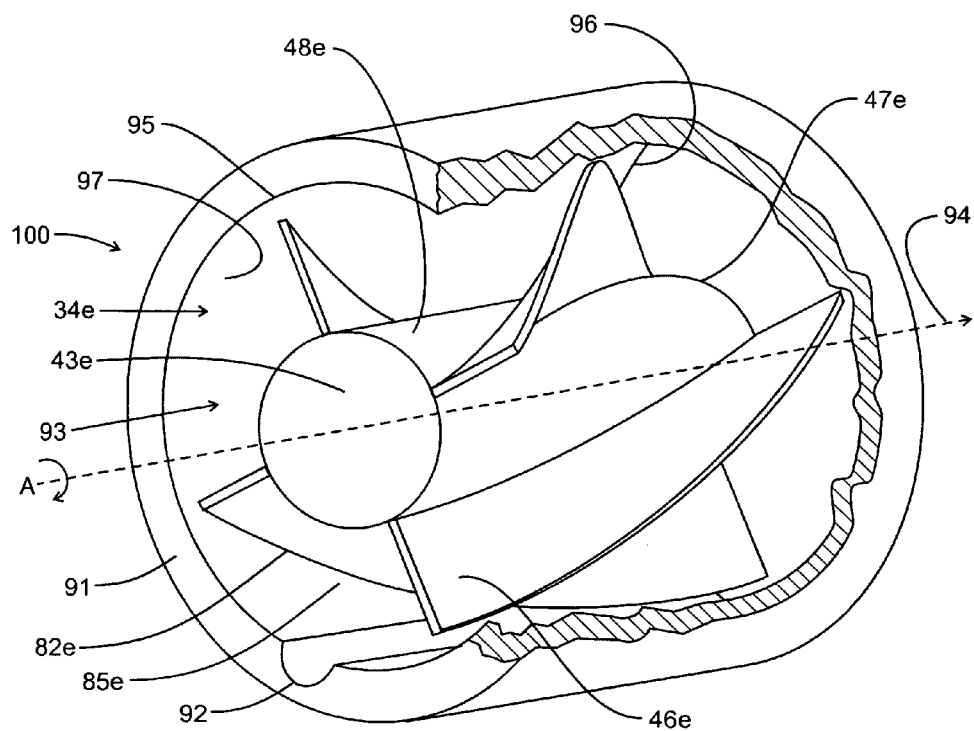

The extractor 34's upstream surface 43 may have any suitable symmetrical profile, which may range from a flat profile, like the profile of the upstream surface 43a of extractor 34a of FIGS. 10-17; to a convex profile, like the profile of the upstream surfaces 43c, 43d, 43e of extractors 34c, 34d, 34e of FIGS. 5, 7 and 8, respectively; to any suitable tapered profile, like the upstream surface 43 of extractor 34 of FIGS. 2-3, like the upstream surface 43b of extractor 34b of FIG. 4, or like the upstream surface 43f of extractor 34f of FIGS. 6 and 9. The upstream portion of a tapered profile may be flat, blunt, rounded, or tapered to a point. The extractors 34, 34b, and 34c illustrated in FIGS. 2-5 are the same, except for the profiles of their respective upstream surfaces 43, 43b, and 43c.

Because an extractor 34 having an upstream surface 43 with a tapered profile is more aerodynamic than one having a non-tapered profile, a tapered profile may offer the advantage of allowing the gaseous stream to flow around the extractor 34 with less drag, and thus with less of a pressure drop. However, a tapered profile may also result in less impingement of entrained liquid particulates on a tapered upstream surface 43, and thus an increased need to extract entrained liquid particulates from the gaseous stream while it is flowing over the extractor 34's side surface 48, downstream surface 47 and downstream features, such as its vanes 46.

During operation of the extraction device 10, the extractor 34's vanes 46 are, of course, rotating at the same rpm as the extractor 34's upstream surface 43. Accordingly, as has been explained above, the vanes 46 may be expected to collect liquid particulates on their surfaces through impingement. These will coalesce into a thin film of extracted liquid that, in turn, forms droplets of extracted liquid at each vane 46's outer edge 82, due to the centrifugal force generated by the rotation of the vanes 46. This centrifugal force, which is at a maximum at the outer edge 82 of each vane 46, may then cause these droplets of extracted liquid to be flung radially outward and strike the extraction duct 17's inner surface 41, where they may then run down the inner surface 41 under the influence of gravity into the pool 30 of extracted liquid.

Depending on the equipment with which the extraction device 10 is to be used, one approach for extracting entrained liquid particulates from a gaseous stream may be preferred over another.

For example, when removing entrained water particles from the steam driving a turbine it may be desirable to use an extractor 34 having a upstream surface 43 with a tapered profile, to reduce the pressure drop caused by the upstream surface 43, and to reduce the impingement rate of high velocity water particles on the upstream surface 43, in order to minimize surface erosion of the upstream surface 43 that might otherwise be caused by the high velocity water particles. Removal of the water particles from the gaseous stream (i.e., from the steam) may be maximized while the steam is flowing over the extractor 34's side surface 48, downstream surface 47 and downstream features, such as its vanes 46, by maximizing direct transfer of the water particles in the steam to the inner surface 41 of the extraction duct 17. This may be done by maximizing the rotational energy given to the steam entering the extraction duct 17 through the source duct 16, such as by maximizing the rotational rate of extractor 34; decreasing the radial gap between the vanes 46 and the inner surface 41; and increasing the longitudinal length of extractor 34, so as to prolong the contact time between the swirling steam and the inner surface 41. Macroscopic swirling of the steam may be augmented by incrementally increasing, in an axial direction, the radial gap between the vanes 46 and the inner surface 41, so as to form an annular diverging nozzle profile from the perspective of the flowing steam.

On the other hand, in a wetted surface air sampler, such as the air sampler 11, it may be advantageous to use an extractor 34*a* having a upstream surface 43*a* with a planar profile (see FIGS. 10-17), rather than the curved or tapered profiles shown in FIGS. 2-9, despite the increased pressure drop a flat upstream profile causes. This is because a flat profile may desirably increase the impingement rate of the water particles on the upstream surface 43*a*, thereby increasing the efficiency with which it extracts the water particles from the gaseous stream.

In any event, management of the thin films of extracted liquid on the extractor 34's upstream surface 43 and on the surfaces of the vanes 46 may also be influenced through the selection of the material from which those surfaces are made, or coated with. For example, if the liquid particulates in the gaseous stream are water particles, then it may be possible to use a hydrophobic material such as Teflon, silicone rubber, or a hydrocarbon wax to make those surfaces less adherent, thereby resulting in less retention of the extracted water by those surfaces; or to create on those surfaces wetting and non-wetting surface areas that impede or direct transport of the extracted water over those surfaces. An upstream surface 43*a* with a flat profile may be advantageous in this context since it allows the creaseless application of film coatings, such as fluorinated polymer films with hydrophobic surfaces, to the upstream surface 43*a* that may have unusual and favorable properties.

A brief summary of the general operation of the extraction device 10 will now be given. Its operation will be at least generally the same, regardless of the kind of device that it is installed in or used with. During operation of the extraction device 10, its extractor 34 may rotate and may be located in the gaseous stream that exits from the source duct 16. At least some of the liquid particulates in the gaseous stream may impact on the extractor 34's upstream surface 43, side surface 48 and vanes 46, to form a thin film of extracted liquid thereon. Such impacts may occur, at least in part, because of the sinuous path that the gaseous stream must follow as it detours around the extractor 34, and because of the unique swirling flow pattern in the gaseous stream around the extractor 34 that may be caused by rotation of the extractor 34.

The centrifugal forces generated by the rotating extractor 34 may cause the thin film of extracted liquid on its upstream surface 43, side surface 48 and vanes 46, to travel radially outward across the upstream surface 43 to its periphery 44, and radially outward across the vanes 46 to their radially outer edges 82, from which the extracted liquid may then be flung (in the form of droplets of extracted liquid) onto the extraction duct 17's inner surface 41, or onto the source duct 16's inner surface 33, depending on the location of the extractor 34 and its upstream surface 43.

The unique swirling flow pattern in the gaseous stream around the extractor 34 may also cause an increased number of the liquid particulates in the gaseous stream to be deposited as extracted liquid directly on the extraction duct 17's inner surface 41, than would otherwise be the case. Regardless of its source, the extracted liquid on the inner surface 41, may then travel sequentially down the inner surface 41 under the force of gravity, into the pool 30 in the reservoir 21, and into the extracted liquid output conduit 23.

If liquid particulates impinging on the inner surface 41 do not wet that surface well, they might effectively create an undesirable reservoir of non-circulating immobile droplets of extracted liquid that adhered to the inner surface 41. However, the rotating flow of the gaseous stream in extraction duct 17 is also beneficial because it would urge such otherwise immobile droplets of extracted liquid to move in a spiral pattern on the inner surface 41, thereby encouraging their coalescence into droplets of extracted liquid so large that they may then travel down the inner surface 41 to the pool 30 in the reservoir 21.

Alternatively, the extracted liquid may be removed from the extraction duct 17 in any other suitable way, such as through holes or slots in the sidewall of the duct 17. Alternatively, if the duct 17 were oriented horizontally, rather than vertically, then its lowest part may act as a reservoir 21 for the pool 30, and the liquid output conduit 23 may be connected to such a reservoir 21 to remove the extracted liquid from the duct 17.

The extracted liquid may then be dealt with in any suitable way, such as by being recycled through, or removed from, the device with which the extraction device 10 is used.

Turning now to FIGS. 7 and 8, they illustrate second and third embodiments 90, 100 of the extraction device of the present invention. It is understood that the extraction devices 10, 60, 90 100 and 110, and their various respective components are the same as each other, or are at least similar to each other, in any particular respect such as with respect to their respective mountings, locations, parts, quantities (how many), sizes, shapes, designs, materials, compositions, constructions, manufactures, physical properties, dimensions, specifications, variations, operations, methods, and uses, except for those differences which will be made apparent by all of the disclosures herein.

Accordingly, for clarity and simplicity, certain parts of the extraction device 90 have been given the same reference numerals, with an "d" suffix, as the reference numerals used for the corresponding respective parts of the extraction device 10, and certain parts of the extraction device 100 have been given the same reference numerals, with an "e" suffix, as the reference numerals used for the corresponding respective parts of the extraction device 10.

The extractors 34*d*, 34*e* may be either a free spinning extractor 34*d*, 34*e* or a powered extractor 34*e*, 34*e*. The extractors 34*d*, 34*e* are illustrated as being mounted entirely within an extraction duct 91, which may be of at least generally uniform diameter, and have an inlet 95 and an outlet 96. The duct 91 may be at least generally the operational equivalent of either a source duct 16 or an extraction duct 17 for the extraction device 10 of FIG. 2. If the duct 91 is considered to be a source duct 16, then there may be a larger diameter extraction duct 17 located downstream from the duct 91. On the other hand, if the duct 91 is considered to be an extraction duct 17, then there may be a smaller diameter source duct 16 located upstream from the duct 91. Alternatively, the duct 91 may be used alone, in the sense that there may not be an operationally separate source duct 16 or extraction duct 17 with which it is used.

The gaseous stream entering the duct 91's inlet 95 in the direction of arrow 93, and exiting the duct 91's outlet 96 in the direction of arrow 94 may, or may not, have a rotational component with respect to the longitudinal axis A of the duct 91 and the extractors 34*d*, 34*e* as it enters the inlet 95. The axis A may be oriented horizontally, vertically, or at any angle therebetween. In addition, the longitudinal axes A of the extractors 34*d*, 34*e* and their respective extraction ducts 91 may not be coincident with each other.

The extractors 34*d*, 34*e* may be free spinning extractors 34*d*, 34*e* or powered extractors 34*d*, 34*e*. The extractors 34*d*, 34*e* may be termed "axial" extractors 34*d*, 34*e* since the flow of the gaseous stream through the channels 85*d*, 85*e* between their respective vanes 46*d*, 46*e* may be generally along their respective axis A.

The vanes 46d, 46e may be located on the side surface 48d, 48e of the extractors 34d, 34e. As an alternative, or in addition, vanes 46d, 46e may be placed on their respective upstream surfaces 43d, 43e, or on their respective downstream surfaces 47d, and 47e. There may be fewer, or more, of the vanes 46d, 46e than those illustrated in FIGS. 7-8. The vanes 46d, 46e may have any suitable size and shape, such as is illustrated in FIGS. 7-8.

The upstream surfaces 43d, 43e and downstream surfaces 47d, 47e of the extractors 34d, 34e, may be of any suitable size and shape. For example, the diameter of the respective side surfaces 48d, 48e of the extractors 34d, 34e may, or may not, be equal to the diameter of their respective upstream surfaces 43d, 43e and downstream surfaces 47d, 47e.

It may be preferred that the vanes 46d, 46e be sized so that their outer edges 82d, 82e are near to, or touch, the duct 91's inner surface 97, so that the amount of the gaseous stream that passes through the channels 85d, 85e between the vanes 46d, 46e may be maximized, or so that the outer edges 82d, 82e of the vanes 46d, 46e may help to sweep any extracted liquid on the duct 91's inner surface 97 into the collection channel 92. Alternatively, the vanes 46d, 46e may be sized so that their outer edges 82d, 82e are spaced further away from the inner surface 97.

Turning again to FIG. 7, by way of example the axial extractor 34d may be a free spinning axial extractor 34d which may be mounted for rotation within the duct 91 in any suitable way, such as is described herein regarding the extractors 34 or 34a. The extractor 34d may be caused to rotate on its axis A by the gaseous stream passing through the duct 91 in any suitable way, such as by providing any suitable number of any suitable vanes 46d on its side surface 48d that interact with the gaseous stream. Rotation may, for example, be created if the gaseous stream expands or contracts in cross-sectional area over the axial extent of vanes 46d, such as if the inner diameter of the duct 91 expanded or contracted in cross sectional area over the axial extent of vanes 46d. By way of further example, rotation of the extractor 34d may be caused by mounting the vanes 46d in a helical pattern, such as shown by the vanes 46e of the extractor 34e of FIG. 8. Alternatively, the extractor 34d may be a powered axial extractor 34d.

During operation of the extraction device 90, the liquid particulates in the gaseous stream passing though the duct 91 may impact on its extractor 34d's rotating upstream surface 43d and vanes 46d, form a thin film of extracted liquid thereon, and then be flung in the form of droplets of extracted liquid by centrifugal force to the duct 91's inner surface 97, where they may then travel down into the collection channel 92 under the force of gravity, or where they may then be swept into the collection channel 92 by the outer edges 82d of the vanes 46d, or by the strong shear forces created by the outer edges 82d if the outer edges 82d do not touch the inner surface 97. The collection channel 92 may be connected to any suitable device to remove or recycle the extracted liquid, such as the output conduit 23 seen in FIGS. 1-2. If desired, liquid may be added to the duct 91 in any suitable way, such as by being sprayed into the gaseous stream entering its inlet 95, or by being added through a supply conduit 22 in its sidewall (not illustrated in FIG. 7 for clarity).

Turning again to FIG. 8, by way of example the axial extractor 34e may be a powered axial extractor 34e that may be powered and mounted for rotation within the duct 91 in any suitable way, such as is described herein regarding the extractors 33 or 34a. Alternatively, the axial extractor 34e may be a free spinning axial extractor 34e.

During operation of the extraction device 100, liquid particulates in the gaseous stream passing though the duct 91 may impact on its extractor 34e's rotating upstream surface 43e and vanes 46e, form a thin film of extracted liquid thereon, and then be flung as droplets of extracted liquid by centrifugal force from them to the duct 91's inner surface 97, where they may then travel down into the collection channel 92 under the force of gravity, or where they may then be swept into the collection channel 92 by the outer edges 82e of the vanes 46e, or by the strong shear forces created by the outer edges 82e if the outer edges 82e do not touch the inner surface 97. The collection channel 92 may then be connected to any suitable device to remove or recycle the extracted liquid, such as the output conduit 23 seen in FIGS. 1-2. If desired, liquid may be added to the duct 91 in any suitable way, such as by being sprayed into the gaseous stream entering its inlet 95, or by being added through a supply conduit 22 in its sidewall (not illustrated in FIG. 8 for clarity).

The powered axial extractor 34e may, by itself, force the gaseous stream to flow through the duct 91, or it may assist in forcing the gaseous stream to flow through the duct 91. In addition, the powered axial extractor 34e may cause the gaseous stream to rotate, thereby causing some of the liquid particulates in the gaseous stream to impact on the duct 91's inner surface 97, where they may then become extracted liquid and travel down into the collection channel 92 under the force of gravity, or where they may then be swept into the collection channel 92 by the outer edges 82e of the vanes 46e, or by the strong shear forces created by the outer edges 82e if the outer edges 82e do not touch the inner surface 97.

Referring now to FIG. 9, it illustrates a fourth embodiment of the liquid particulate extraction device 110 of the present invention that is shown, by way of example, installed in the air sampler 11 of FIG. 1. In FIG. 9, the fan 18 of the air sampler 11 is not illustrated, for simplicity; but the fan 18 may be mounted to the top 114 of the mounting sleeve 112 that is seen in FIG. 9.

It is understood that the extraction devices 10, 60, 90 100 and 110, and their various respective components are the same as each other, or are at least similar to each other, in any particular respect such as with respect to their respective mountings, locations, parts, quantities (how many), sizes, shapes, designs, materials, compositions, constructions, manufactures, physical properties, dimensions, specifications, variations, operations, methods, and uses, except for those differences which will be made apparent by all of the disclosures herein.

Accordingly, for clarity and simplicity, certain parts of the extraction device 110 have been given the same reference numerals, with an "f" suffix, as the reference numerals used for the corresponding respective parts of the extraction device 10.

Turning again to FIG. 9, the extraction device 110 may comprise a rotating extractor 34f (seen in more detail in FIG. 6), which has an exterior surface that may comprise an upstream surface 43f, a periphery 44f, a side surface 48f, a downstream surface 47f and a re-entrainment preventer 78f. The extractor 34f may be either a free spinning extractor 34f or a powered extractor 34f.

The extraction device 110 may further comprise any suitable extractor mount that mounts the extractor 34f in any desired location in the source or extraction ducts 16, 17, such as the extractor mount 59f. The extractor mount 59f may comprise, for example, a mounting shaft 35f for the extractor 34f and a spider 36f for mounting the shaft 35f. The spider 36f may comprise a hub 37f and an adapter 39f. The mounting sleeve 112 may be of any suitable size and shape for mounting the spider 36f's adapter 39f to the upper portion of the extraction duct 17.

The extraction device 110 may further comprise part or all of the air sampler 11's source and extraction ducts 16, 17; and any suitable output device for removing from the source and extraction ducts 16, 17 the extracted water that has been extracted from the air stream by the extractor 34f, such as the extracted water output conduit 23.

As seen in FIG. 9, in a case where the outlet 45f of the extraction duct 17 has a diameter that is less than the diameter of the portion of the duct 17 that is near the periphery 44*f* of the extractor 34*f*, then the extractor 34*f* may be mounted near the outlet 45*f* so that part or all of the downstream edges 84*f* of its vanes 46*f* overlap the duct 17's surface 116, and are located near, or touch, the surface 116. With the construction shown in FIG. 9 the vanes 46*f* may be particularly effective in collecting liquid particulates from the gaseous stream and flinging them as droplets of extracted liquid onto the duct 17's inner surface 41 if the extractor 34*f* and the duct 17's outlet 45*f* are sized and located with respect to each other so that at least most, or all, of the gaseous stream in the duct 17 is forced to flow through the channels 85*f* between the vanes 46*f* before exiting through the duct 17's outlet 45*f*. For example, the maximum cross sectional area of the extractor 34*f* may be selected to be at least about equal to, or greater than, the inner cross sectional area of the duct 17's outlet 45*f*; the extractor 34*f* may be located near the outlet 45*f*; and the size of the vanes 46*f* on the extractor 34*f*'s downstream surface 47*f* may be selected so that their radially outermost edges 82*f* overlap, or extend radially outward past, the outlet 45*f*; and the downstream edges 84*f* of the vanes 46*f* may be located near, or touching, the duct 17's surface 116.

Flow of the gaseous stream through the channels 85*f* between the vanes 46*f* is characterized by its having axial and radially inward velocity components; as well as a circumferential component caused by the rotation of the vanes 46*f*. In total, these conditions create shearing-type impingement of the gaseous stream on the surfaces of the vanes 46*f*, and enhanced transfer of liquid particulates in the gaseous stream onto the vanes 46*f* and downstream surface 47*f* to form thin films of extracted liquid thereon, which are then flung as droplets of extracted liquid onto the inner surface 41 of the extraction duct 17, where they may then travel into the pool of extracted liquid 30*f*.

Specific design and operating choices must be made in order to obtain favorable high extraction rates of the liquid particulates from the gaseous stream by the vanes 46*f* when extractor 34*f* is operated so that the gaseous stream is forced to pass through the channels 85*f* between its vanes 46*f*. For example, locating the vanes 46*f* so that their downstream edges 84*f* are near, or touching, the duct 17's surface 116 will minimize leakage therebetween of the gaseous stream, of any liquid particulates carried by the gaseous stream, and of any liquid film or droplets present on the surface 116.

As seen in FIGS. 6 and 9, the extractor 34*f* may further comprise a thin annular stiffening plate 86 that is secured to one or more of the downstream edges 84*f* of the vanes 46*f*. The radial width of the annular plate 86 may be selected to be at least about equal to the radial width of the portions of the downstream edges 84*f* that overlap the duct 17's surface 116, although its radial width may be greater or smaller than this amount. The plate 86's downstream surface 87 may be near, or touching, the inner surface 97 in total or in one or more radial zones, to minimize or effectively eliminate any flow of the gaseous stream, and the liquid particulates it carries, through any gap between the adjacent rotating and fixed surfaces 87 and 116, respectively. To minimize viscous and frictional losses due to the close proximity or contact of downstream surface 87 and surface 116, the annular plate 86 may extend vertically at its inner and outer diameters to form dual annular flanges 88 that are parallel to and in close proximity to, or touch, the surface 116. Although two flanges 88 are illustrated, there may be only one flange 88, or more than two flanges 88.

The plate 86 and surface 116 may have any other suitable and mutually compatible shapes, such as each being part of a cone or a sphere. The primary criteria may be that the plate 86 and the surface 116 have corresponding shapes that enable them to be placed close to, or touching each other, in at least one radial annular area, to minimize leakage therebetween of the gaseous stream, of any liquid particulates carried by the gaseous stream, and of any liquid film or droplets present on the surface 116.

With such a construction, in order for the gaseous stream to exit the extraction duct 17, it must flow through the channels 85*f* between the extractor 34*f*'s vanes 46*f*. Each channel 85 may have a downstream surface defined by the plate 86, an upstream surface defined by the extractor 34's downstream surface 47, and a pair of side surfaces defined by the adjacent pair of vanes 46*f*. With such a design approach the majority of liquid particulates entering the channels 85*f* between the rotating vanes 46*f* are moving at a rotational velocity similar to that of the vanes 46*f*, which may provide the benefit of minimizing damage to any sensitive target organisms in the liquid particulates entrained in the gaseous stream that are captured by the extractor 34*f*'s vanes 46*f* as extracted liquid.

Without plate 86, liquid particulates from the gaseous stream could directly impact on the duct 17's surface 116, and form a thin film of extracted liquid on the surface 116. In addition, flow of the gaseous stream through the channels 85*f* between the vanes 46*f* could urge part of the film of extracted liquid already on the vanes 46*f* to travel towards the top of the vanes 46*f* and onto the surface 116. Such extracted liquid on the surface 116 may then be entrained in the fast-moving gaseous stream exhaust gas through shear and gas entrainment processes, and lost to the fan 18. While placing the vanes 46 in close proximity to the surface 116 may assist in reducing such losses, it is unlikely that such losses will be eliminated by such an expedient.

Plate 86 and its downstream surface 87 or its upraised dual annular flanges 88 may serve the desirable function of minimizing the coalescing of liquid particulates onto the portion of the surface 116 that is above the plate 86 by substantially reducing, or effectively eliminating, the amount of the gaseous stream that flows between the plate 86 and surface 116. It has been discovered that when the surface 116 and the downstream surface 87 or flanges 88 are positioned close to, or touching, each other, and when sufficient liquid particulates are present in the gaseous stream, the liquid particulates may coalesce and form a liquid seal between the surface 116 and the downstream surface 87 or flanges 88. When this occurs flow of the gaseous stream through any space between the plate 86 and surface 116 may be reduced by the liquid seal to a negligible level. In any event, the rapidly rotating plate 86 and vanes 46*f* will tend to desirably fling any film of extracted liquid on the plate 86 and vanes 46*f* radially outward as droplets of extracted liquid onto the duct 17's inner surface 41, where they may then travel down under the influence of gravity into the pool 30*f* of extracted liquid; rather than the extracted liquid being lost by being carried by the gaseous stream through the channels 85*f* between the vanes 46*f* and into the duct 17's outlet 45*f*.

In general, the size and profile of any gap between the surface 116 and the plate 86 or flanges 88 may be selected such that air shear forces exerted by the gaseous stream on any thin film of extracted liquid within the gap will not cause the thin film to be pushed into the duct 17's outlet 45. The maximum tolerable size of the gap may vary, depending on such variables as the amount of fluid loss that can be tolerated for the equipment with which the extraction device 110 is used, the wetting angles of the extractor 34f and surface 116, the RPM of the extractor 34f, the gap profile, and the pressure drop across the extractor 34f's vanes 46f. Thus, the maximum tolerable size of the gap may best be determined empirically for any particular specific design.

Figure 10:
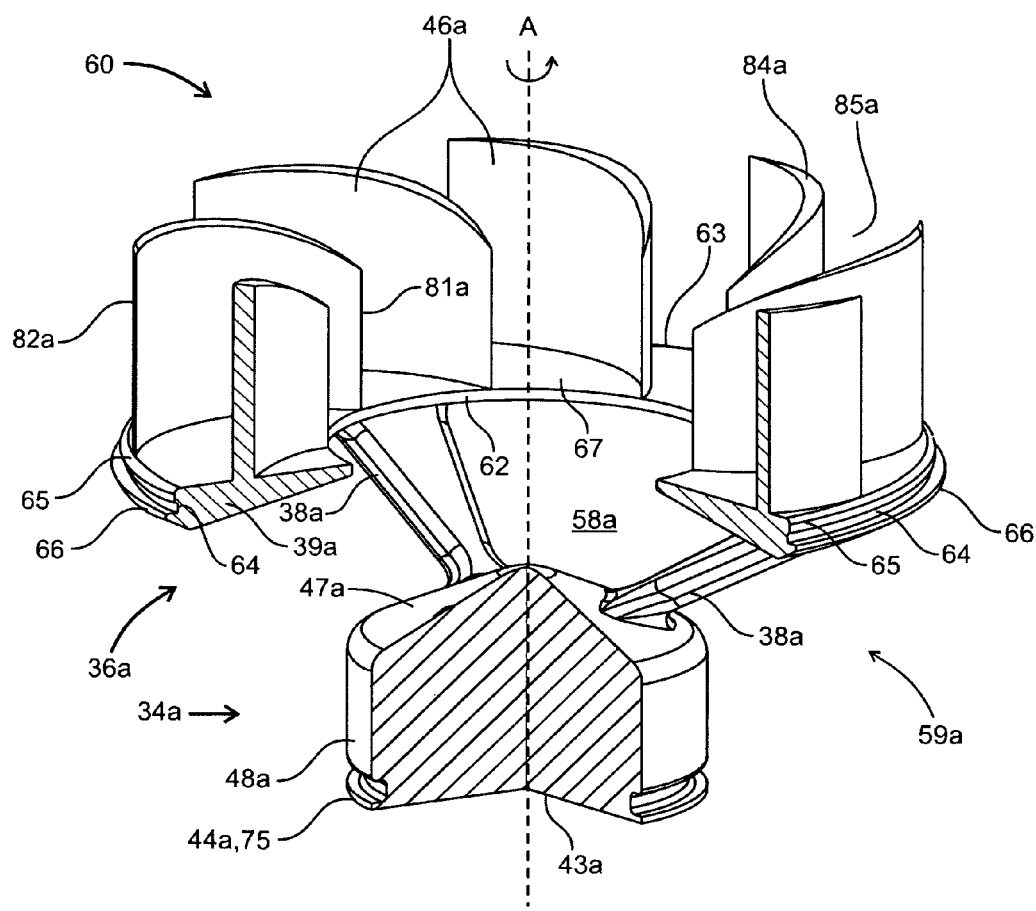
FIG. 10 is a is a side perspective view of a fifth embodiment of the liquid particulate extraction device of the present invention, shown partly in cross-section.
Figure 11:
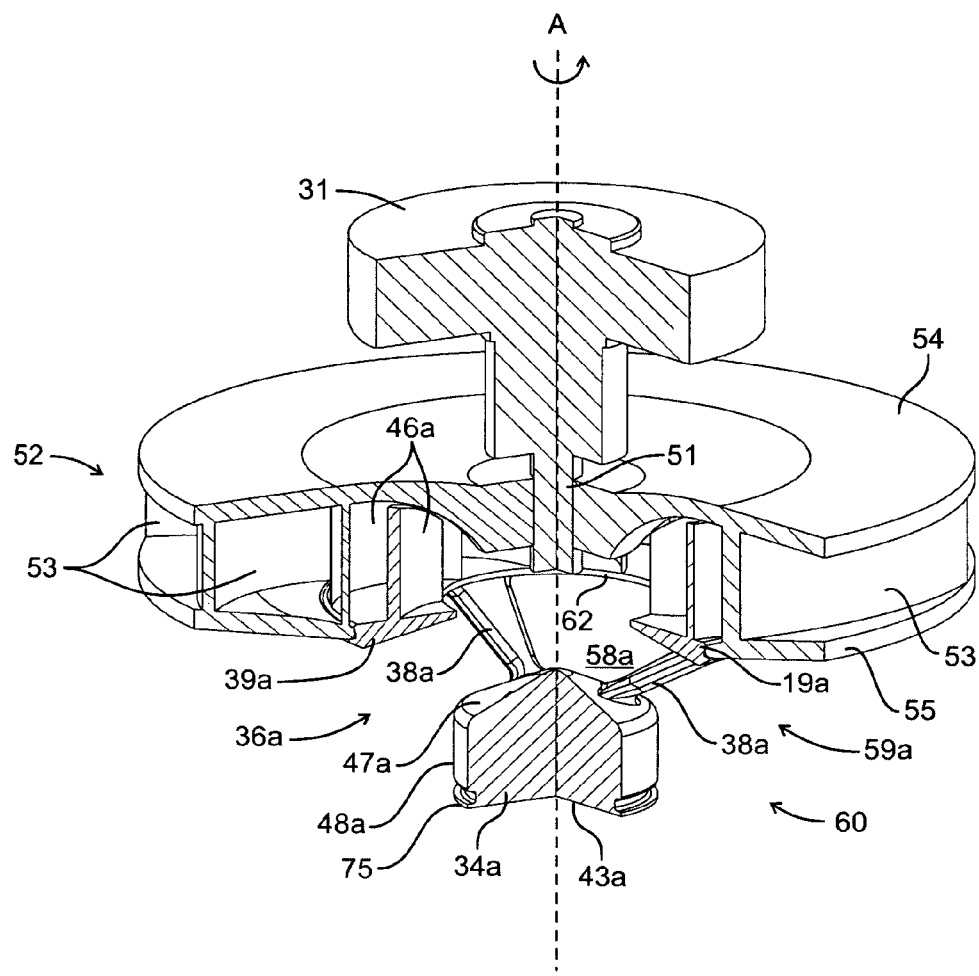
FIG. 11 is a side perspective view, partly in cross-section, of the fifth embodiment shown installed in a fan rotor's air inlet.
Figure 12:
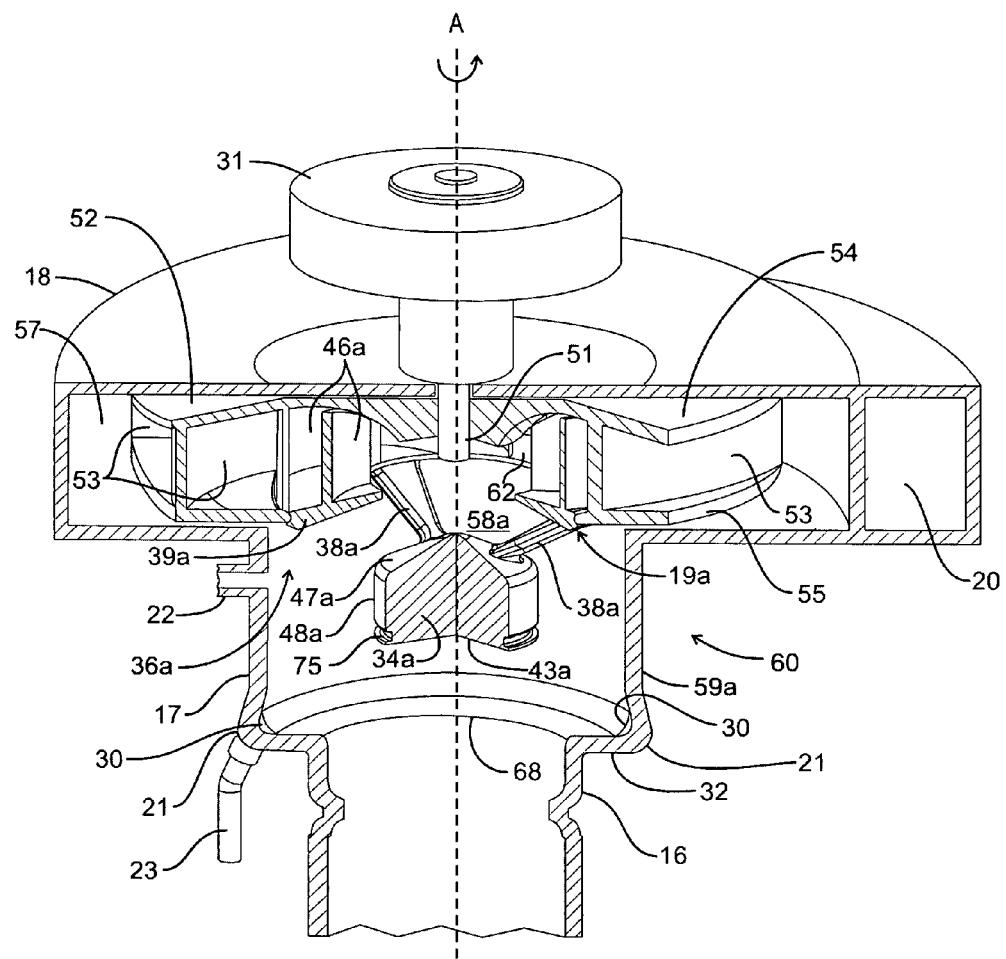
FIG. 12 is a side perspective view, partly in cross-section, of the fifth embodiment shown installed in the air sampler of FIG. 1, with part of the air sampler being broken away.
Figure 13:
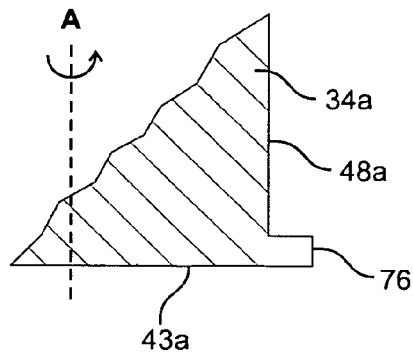
FIGS. 13-17 are cross sectional views of alternative forms of re-entrainment preventers for the extractors, with part of the extractors being broken away.
Figure 14:
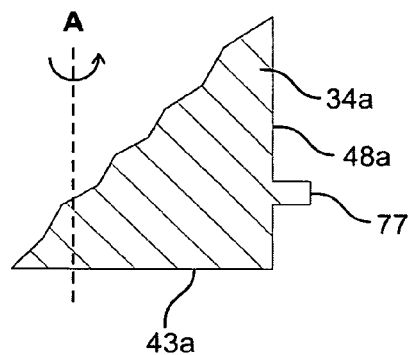
Figure 15:
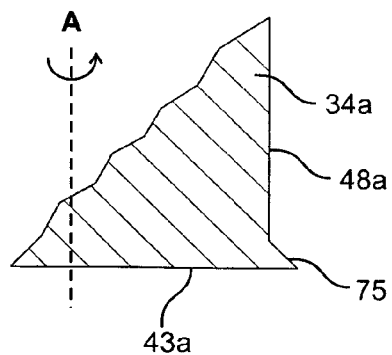
Figure 16:
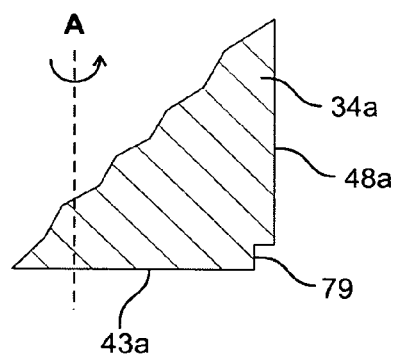
Figure 17:
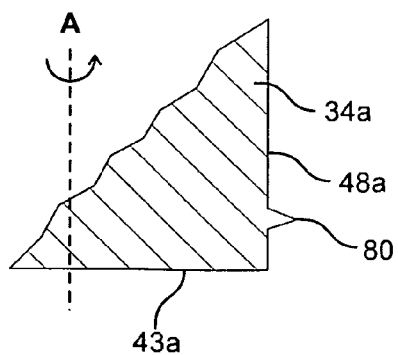

Turning now to FIGS. 10-12, they illustrate a fifth embodiment 60 of the extraction device of the present invention. It is understood that the extraction devices 10, 60, 90, 100 and 110, and their various respective components are the same as each other, or are at least similar to each other, in any particular respect such as with respect to their respective mountings, locations, parts, quantities (how many), sizes, shapes, designs, materials, compositions, constructions, manufactures, physical properties, dimensions, specifications, variations, operations, methods, and uses, except for those differences which will be made apparent by all of the disclosures herein. Accordingly, for clarity and simplicity, certain parts of the extraction device 60 have been given the same reference numerals, with an "a" suffix, as the reference numerals used for the corresponding respective parts of the extraction device 10.

The extraction device 60 is illustrated in FIG. 12, by way of example, as being installed in the wetted surface air sampler 11 of FIG. 1. The air sampler 11 may use any suitable fan 18 for drawing air through its source duct 16 and extraction duct 17. As seen in FIGS. 11-12, the fan 18 may comprise, for example, any suitable fan motor 31 and any suitable fan rotor 52 that may be secured to the fan motor 31's drive shaft 51 in any suitable way, so that the fan motor 31 may drive the fan rotor 52 to rotate. The fan rotor 52 may be, for example, of the closed "box" style wherein the fan rotor 52's vanes 53 may be mounted between upper and lower circular cross-section faceplates 54, 55. The lower faceplate 55 on the fan rotor 52's air inlet side may have a centrally-located air inlet 19a, while air may be discharged from the fan rotor 52's outside perimeter into a volute structure 57 that conveys it to the fan 18's air outlet 20.

The extraction device 60 may comprise a powered rotating extractor 34a and any suitable extractor mount 59a that mounts the extractor 34a in any desired location in the source or extraction ducts 16, 17.

The extraction device 60 may further comprise part or all of the air sampler 11's source and extraction ducts 16, 17, and any suitable extracted water output device, such as the extracted water output conduit 23, that removes the extracted water from the source and extraction ducts 16, 17.

The extraction device 60 may further comprise any suitable power source for directly or indirectly powering the powered extractor 34a for rotation. For example, the power source may comprise any suitable motor (e.g. the fan motor 31) that is directly connected to the powered extractor 34a. Alternatively, any suitable motor may be indirectly connected to the powered extractor 34a. For example, the power source may comprise any suitable motor, such as the fan motor 31, and may further comprise any suitable equipment for indirectly connecting the motor 31 to the powered extractor 34a, such as the fan rotor 52 and extractor mount 59a. Any other suitable equipment for indirectly connecting a motor to the powered extractor 34a may be used, such as drive shafts, belts, gears, etc.

The extractor mount 59a may comprise, for example, a spider 36a for mounting the extractor 34a to the fan rotor 52's air inlet 19a, so that the extractor 34a may be powered for rotation by the fan motor 31 through the fan rotor 52. The extractor mount 59a may further comprise the fan rotor 52. The extractor 34a's downstream surface 47a may have a rounded or tapered aerodynamic shape to reduce the pressure drop that the extractor 34a may otherwise cause. The spider 36a may comprise three arms 38a, a peripheral adapter 39a, an air channel 58a defined between each adjacent pair of arms 38a, and an air outlet 62 defined by the peripheral adapter 39a. The air channels 58a and the air outlet 62 may permit the free flow of the gaseous stream as it exits the extraction device 60.

Although the spider 36a is illustrated as having three arms 38a, there may be fewer, or more, arms 38a. The arms 38a may have any suitable size and shape. For example, they may be made in the form of vanes 46a, so that as they are rotated by the fan motor 31 through the fan rotor 52, they may provide some secondary pumping of the gaseous stream passing by them (with the primary pumping being provided by the fan rotor 52), which may help to compensate for the pressure drop that may otherwise be caused by the extraction device 60.

Optional vanes 46a may be provided on the downstream surface 67 of the adapter 39a, to provide some secondary pumping of the gaseous stream flowing through the adapter 39a's air outlet 62 (with the primary pumping being provided by the fan rotor 52), which may help to compensate for the pressure drop that may otherwise be caused by the extraction device 60.

The adapter 39a may serve to mount the arms 38a to the fan rotor 52's inlet 19a, and may have any suitable size, shape and construction. For example, as best seen in FIGS. 10-11, the adapter 39a may have a peripheral mounting groove 64 defined between upper and lower peripheral flanges 65, 66. The adapter 39a, mounting groove 64, and upper and lower peripheral flanges 65, 66 may be sized to form a snap fit with the fan rotor 52's air inlet 19a, with the rim of the air inlet 19a fitting into the mounting groove 64, and with the lower flange 66 being sized large enough to act as a stop to prevent further travel of the adapter 39a into the fan rotor 52's air inlet 19a. Although the adapter 39a, groove 64 and flanges 65, 66 are illustrated as being unbroken, any or all of them may be segmented.

Alternatively, the adapter 39a may be releasably, or non-releasably secured to the fan rotor 52's lower faceplate 55 in any other suitable way, such as by the use of welding, fasteners, adhesives, threads, etc. As a further alternative, the adapter 39a may be eliminated, and the spider 36a's arms 38a may be secured directly to the fan rotor 52's upper or lower faceplate 54, 55 in any suitable way, such as with a snap fit similar to that described above, welding, fasteners, adhesives, threads, etc.

As seen in FIGS. 10-12, the spider 36a's arms 38a may serve to connect the extractor 34a to the adapter 39a, so that the powered rotating extractor 34a is powered for rotation by the fan motor 31 through the fan rotor 52's lower faceplate 55 and the spider 36a. Although the arms 38a are shown connected to the extractor 34a's downstream surface 47a, they may be secured to its side surface 48a.

Thus, it is seen that it has been discovered that the air inlet 19a of this common type of fan rotor 52 may be quickly, easily, and inexpensively used for the dual purposes of acting as a mounting flange for mounting the extraction device 60 within the air sampler 11, as seen in FIG. 12; and as acting as a power source for driving the powered rotating extractor 34a.

Direct or indirect power from a motor for driving the powered rotating extractor 34a may be provided in any other suitable way. For example, if the extractor 34a is driven directly by the fan motor 31, then it may be fixed in any suitable way to the fan motor 31's drive shaft 51, in which case the spider 36a may be eliminated. Alternatively, the powered extractor 34a may be mounted for rotation in any other suitable way within the source and extraction ducts 16, 17. The direct or indirect power from a motor may supplied to the extractor 34a though drive gears, belts, etc.

The extractor 34a's upstream, downstream and side surfaces 43, 47, 48 may be provided with vanes 46a. Because the extractor 34a is powered, any of such vanes may offer the advantage of providing some secondary pumping of the gaseous stream flowing by them (with the primary pumping being provided by the fan rotor 52), which may help to compensate for the pressure drop that may otherwise be caused by the extraction device 60.

As has been mentioned, the gaseous stream travels in a serpentine flow path as it encounters, and then flows around, the extractor 34a. This serpentine flow path may lead to the undesirable re-entrainment by the gaseous stream of liquid particulates captured by the extractor 34a's upstream surface 43a, unless the extractor 34a is properly designed. This is because surface tension forces will tend to cause any extracted liquid that is pooling along the periphery 44a of the upstream surface 43a to be distributed onto the extractor 34a's side surface 48a, downstream surface 47a and downstream features, such as its vanes 46a, where it may be more easily re-entrained by the gaseous stream.

By way of example, let it be assumed that the extractor 34a is in the form of a right circular cylinder that has a height equal to the cross-sectional area of its upstream surface 43a, similar to the extractor 34a of FIGS. 10-12. As such an extractor 34a rotates, the extracted liquid on its upstream surface 43a will be pumped to its periphery 44a by the centrifugal forces created by its rotation, and tend to pool there. Surface tension forces will then cause the pooled extracted liquid to wet and move downstream across the extractor 34a's cylindrical side surface 48a, creating a large uncontrolled area of extracted liquid on the side surface 48a. The transitional profile between the upstream surface 43a and side surface 48a may influence this behavior. If the profile is formed as a large smooth radius, for example, surface tension wetting of the side surface 48a by the extracted liquid may be encouraged. This wetting of the side surface 48a by the extracted liquid may be exacerbated by shear forces created by the gaseous stream flowing past the side surface 48a, which may tend to spread the extracted liquid even further downstream across the side surface 48a.

It has been discovered that providing the extractor 34a with a re-entrainment preventer 75 may effectively prevent such undesirable re-entrainment of the extracted liquid on the extractor 34a's side surface 48a, downstream surface 47a and downstream features, such as its vanes 46a. The re-entrainment preventer 75 may have any suitable size and shape and may be situated on the extractor 34a's side surface 48a in any suitable location, such as seen in FIGS. 10-12.

In general, regardless of the re-entrainment preventer 75's particular size, shape and location, it may be characterized by having an extended portion that extends radially outward a greater or shorter distance from the extractor 34a's longitudinal axis A than do the adjacent portions of the extractor 34a's side surface 48a, so that extracted liquid on the extractor 34a's side surface 48a may tend to be forced to the radially outermost edge of the re-entrainment preventer 75 by the centrifugal force generated by the rotation of the extractor 34a, and thrown onto the extraction duct 17's inner surface 41a, rather than traveling downstream across the extractor 34a's side surface 48a, downstream surface 47a, and downstream features, such as its vanes 46a. In addition, the re-entrainment preventer 75 may be characterized by having an axial length that is at least substantially smaller than the axial length of the extractor 34a's side surface 48a.

The re-entrainment preventer 75 may have any other suitable size, shape and location, such as the re-entrainment preventers 76-77 and 79-80 seen in FIGS. 13-17. Because of their shape and structure, the re-entrainment preventers 76-77 and 79 of FIGS. 13-14 and 16 may be called flange re-entrainment preventers, while the preventers 75 and 80 of FIGS. 15 and 17 may be called knife-edge re-entrainment preventers.

Although the re-entrainment preventers 75-80 are illustrated in the various Figures as extending out at a right angle from the extractor 34a's longitudinal axis A, they may extend out at an angle that is greater than, or less than a right angle. Although it may be preferred that the preventers 75-80 be continuous and completely encircle the extractor 34a's side surface 48a, as an alternative they may not be continuous and may not completely encircle the side surface 48a. Although the preventers 75-80 may follow a path that lies in one plane, the preventers 75-80 may follow a path that does not lie in one plane, e.g., the preventers 75-80 may follow a curved or zigzag path. Although it may be preferred that the preventers 75-80 be part of, or located in close proximity to, the extractor 34a's upstream surface 43a; as an alternative they may be located on any other portions of the extractor 34a's side surface 48a, on its downstream surface 47a or on its downstream features, such as it's the vanes 46a.

In general, all the re-entrainment preventers 75-80 may have narrow profiles that tend to form and discharge extracted liquid droplets radially outward without becoming loaded with excessive extracted liquid, so that they may impede downstream movement of the extracted liquid across the extractor 34a's side surface 48a, downstream surface 47a and downstream features, such as its vanes 46a.

The side surface 48 of the extractor 34 of FIGS. 2-4 may act as a flange reintranement preventer 78. Alternatively, the extractor 34 may be equipped with any suitable re-entrainment preventer 75-76 or 77-80 in any suitable way, such as by making the intersection of its upstream and side surfaces 43, 48 in the form of a flange or knife-edge re-entrainment preventer 75-77 or 79-80. Alternatively, the extractor 34 may be provided with a side surface 48 that is axially elongated more than that illustrated in FIGS. 2-4, to enable the extractor 34 to utilize any of the re-entrainment preventers 75-77 or 79-80.

A series of tests was conducted with the extraction device 60 of FIGS. 10-12 on a piece of equipment similar to the air sampler 11. The source duct 16 was 0.91 cm in diameter, the extraction duct 17 was 3.68 cm in diameter, and the maximum outside diameter of the powered rotating extractor 34a was 1.58 cm. The extractor 34a was positioned so that its upstream surface 43a was located about 0.65 cm above the connector 32 between the source and extraction ducts 16, 17. The extractor 34a's upstream surface 43a was nominally flat, and covered by a hydrophobic fluorocarbon film to minimize attachment of water particles to it. The fan motor 31 spun the extractor 34a at about 14,000 rpm.

Figure 18:
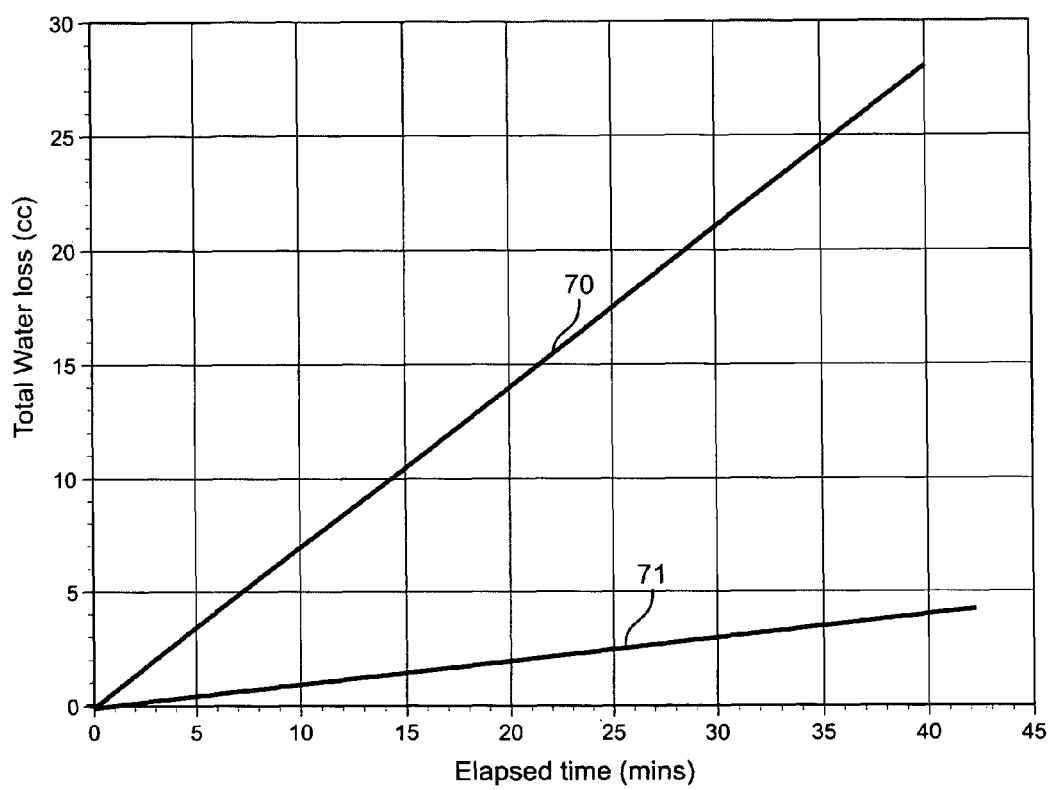
FIG. 18 is a graphical representation of certain test results for the second embodiment.

In FIG. 18, the water loss from the air sampler 11 with and without the extractor 34a is shown. Line 70 shows the water loss from an air sampler 11 having no extractor 34a and a 1.0 cc water inventory, while line 71 shows the average water loss from an air sampler 11 having an extractor 34a, and being tested with water inventories of 0.7 cc, 0.75 cc, 1.15 cc and 1.25 cc. The total water losses shown in FIG. 18 are much greater than the stated water inventories because, as has been mentioned, the liquid level control device 24 maintains the desired water inventory within the air sampler 11 despite any water losses due to evaporation or water particles being expelled from the fan 18's outlet 20.

FIG. 18 shows that use of the extractor 34*a* resulted in a remarkable reduction in the water loss from the air sampler 11 by a factor of about 7 times.

A series of tests was also conducted with the extraction device 10 of FIG. 2 on a piece of equipment similar to the air sampler 11. The source duct 16 was 3.15 cm in diameter, the extraction duct 17 was 4.54 cm in diameter, and the maximum outside diameter of the free spinning rotating extractor 34 was 3.0 cm. The extractor 34 was positioned so that its upstream surface 43 was located about 1.0 cm above the connector 32 between the source and extraction ducts 16, 17. As seen in FIG. 2, the extractor 34's upstream surface 43 was not flat, but had an aerodynamic cross-sectional shape to reduce drag. The flow of the air stream over the vanes 46*a* on the extractor 34's downstream surface 47 created sufficient torque so that the rotating extractor 34 rotated at a rate of about 6,000 rpm when 300 liters per minute of air were flowing through the air sampler 11.

As was discussed above, all wetted surface air samplers, such as the air sampler 11, are subject to a loss process called re-aerosolization, which results in the undesirable loss of solid target particulates that were previous captured by the water within the air sampler 11.

It has been discovered that the extractor 34 is very effective at recapturing some of these re-aerosoled solid particulates that might otherwise be lost by being exhausted from the fan 18's air outlet 20. To determine just how effective the extractor 34 may be in this regard, the air sampler 11 was loaded with a water inventory that contained a dilute suspension of a particulate test material called Arizona Fine Test Dust (AFTD), available from Powder Technology Inc., of Burnsville, Minn. The air sampler 11 was then operated for a period of up to two hours, over which time water samples were periodically removed from the air sampler 11 through its sample conduit 27 to ascertain the amount of AFTD still remaining in the air sampler 11.

Figure 19:
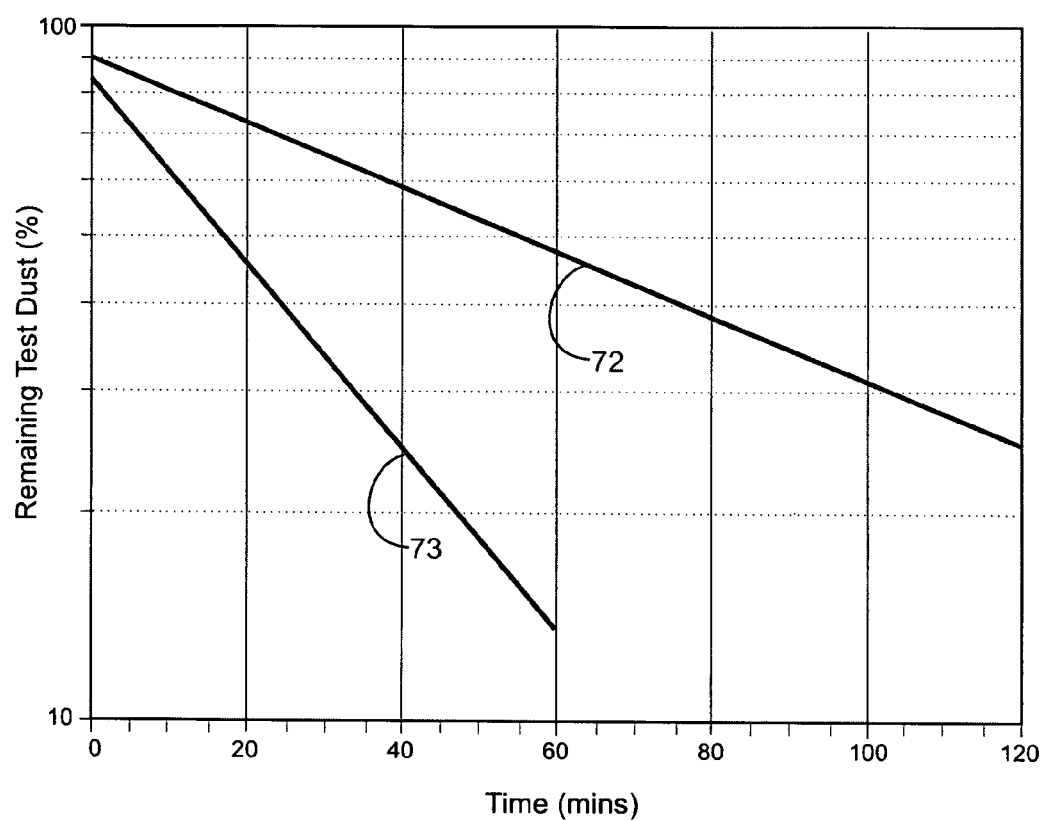
FIG. 19 is a graphical representation of certain test results for the first embodiment.

In FIG. 19, lines 72 and 73 show, respectively, the amount of the original charge of AFTD remaining in the air sampler 11 with and without the extractor 34. From FIG. 19, it can be seen that the amount of the original charge of AFTD remaining in the air sampler 11 without the extractor 34 was about 20% after 50 minutes, whereas with the extractor 34 the air sampler 11 retained more than 20% of the original charge of AFTD for a period of over 120 minutes, which is about a 2.5 times improvement in retention time for the original charge of AFTD.

From the foregoing, it will be appreciated that specific embodiments of the invention have been described herein for purposes of illustration, and that various modifications may be made without deviating from the invention. Additionally, aspects of the invention described in the context of particular embodiments may be combined or eliminated in other embodiments. Although advantages associated with certain embodiments of the invention have been described in the context of those embodiments, other embodiments may also exhibit such advantages. Additionally, not all embodiments need necessarily exhibit such advantages to fall within the scope of the invention.

It is to be understood that any particular part of the invention may be suitably combined or formed with one or more of its other parts to form a composite part; that any particular part of the invention described as being made in one piece may be formed by assembling together in any suitable way, two or more sub-pieces; that the direction of rotation of any rotating parts of the invention may be either clockwise or counterclockwise; and that the various parts of the invention may be assembled together in any suitable ways other than those described herein by using any appropriate means, such as fasteners, welding, adhesives, bonding, threads, friction fits, interference fits, splines, keys, etc.

In addition, when the term "at least one of" is used in any of the claims, that term is defined to mean that any one, any more than one, or all, of the listed things or steps following that term is, or are, part of the claimed invention. For example, if a hypothetical claim recited "at least one of A, B, and C", then the claim is to be interpreted so that it may comprise (in addition to anything else recited in the claim), an A alone, a B alone, a C alone, both A and B, both A and C, both B and C, or all of A, B and C.

The words "means for" must appear in a claim before that claim is construed as claiming a means or step for performing a specified function under 35 USC section 112, sixth paragraph.

It is understood that the foregoing forms of the invention were described and illustrated strictly by way of non-limiting example. As used herein, except in the claims, the words "and" and "or" are each defined to also carry the meaning of "and/or".

In view of all of the disclosures herein, these and further modifications, adaptations and variations of the present invention will now be apparent to those of ordinary skill in the art to which it pertains, within the scope of the following claims.

What is claimed is:

1. An extraction device for extracting entrained liquid particulates from a gaseous stream, wherein said extraction device comprises:

an extractor; an extraction duct; and an extractor mount that is operable to mount said extractor for rotation at least partially within said extraction duct;

wherein said extractor comprises an upstream end and an exterior surface; wherein said exterior surface comprises an upstream surface, and wherein said upstream surface comprises a periphery;

wherein said extractor's upstream end does not comprise an inlet that is operable to receive said gaseous stream; wherein said extractor does not comprise an interior central space that is operable to receive said gaseous stream from said inlet; and wherein said gaseous stream does not travel radially outwardly through said extractor from said interior central space to outside of said extractor;

wherein said extraction duct comprises an inner surface and an extracted liquid outlet; and wherein, during use of said extraction device, said gaseous stream passes through said extraction duct; said extractor is immersed within said gaseous stream, said extraction device rotates, and at least some of said liquid particulates in said gaseous stream are extracted from said gaseous stream by said upstream surface of said extractor and form a thin film of extracted liquid on said upstream surface; wherein as said extractor rotates it creates a centrifugal force that urges said extracted liquid on said upstream surface to travel to said periphery of said upstream surface and to be flung from said periphery to said inner surface of said extraction duct; and wherein at least some of said extracted liquid on said inner surface of said extraction duct travels to said extracted liquid outlet.

2. The extraction device of claim 1, wherein said extractor is a powered extractor, and wherein said extraction device further comprises a power source that is operable to drive said powered extractor to rotate during use of said extraction device.

3. The extraction device of claim 2, wherein said powered extractor further comprises a vane that is carried by said exterior surface of said powered extractor; and wherein said vane interacts with said gaseous steam to urge said gaseous stream to flow.

4. The extraction device of claim 3, wherein said vane has an outer edge; wherein during use of said extraction device at least some of said liquid particulates in said gaseous stream are extracted from said gaseous stream by said vane to form a thin film of extracted liquid on said vane; and wherein as said powered extractor rotates it creates a centrifugal force that urges said extracted liquid on said vane to travel to said outer edge of said vane and to be flung from said outer edge to said inner surface of said extraction duct.

5. The extraction device of claim 4, wherein said exterior surface of said powered extractor further comprises a side surface, and wherein said vane is carried by said side surface of said powered extractor.

6. The extraction device of claim 5, wherein said side surface of said powered extractor is axially elongated; and wherein said vane is axially elongated and is sized to be a close fit with said inner surface of said extraction duct, to at least minimize an amount of said gaseous stream that passes between said outer edge of said vane and said inner surface of said extraction duct.

7. The extraction device of claim 6, wherein said extraction duct further comprises an extracted liquid channel that is at least partially defined by said inner surface of said extraction duct; and wherein at least some of said extracted liquid on said inner surface of said extraction duct travels through said extracted liquid channel to said extracted liquid outlet.

8. The extraction device of claim 2, wherein said power source comprises a fan motor and a fan rotor having an air inlet; wherein said extractor mount is operable to connect said powered extractor to said air inlet; and wherein said fan motor drives said powered extractor to rotate through said fan rotor and said extractor mount.

9. The extraction device of claim 8, wherein said extractor mount comprises an adapter having a peripheral mounting groove; and wherein said mounting groove has a snap fit with said air inlet of said fan rotor.

10. The extraction device of claim 1, wherein said extractor further comprises a re-entrainment preventer.

11. The extraction device of claim 10, wherein said re-entrainment preventer is a knife-edge re-entrainment preventer.

12. The extraction device of claim 10, wherein said re-entrainment preventer is a flange re-entrainment preventer.

13. The extraction device of claim 1 wherein, during use of said extraction device, said gaseous stream comprises a gaseous vortex that has a rate of rotation and said extractor has a rate of rotation; and wherein said rate of rotation of said extractor and said rate of rotation of said gaseous vortex are selected to be at least about equal to each other, to minimize a force with which said liquid particulates impact on said upstream surface of said extractor.

14. The extraction device of claim 1, wherein said gaseous stream flows in a serpentine flow path around said extractor during use of said extraction device; wherein said serpentine flow path increases a rate at which said liquid particulates are extracted from said gaseous stream by said upstream surface of said extractor, and also increases a rate at which said liquid particulates are extracted from said gaseous stream by said inner surface of said extraction duct.

15. The extraction device of claim 1, wherein said gaseous stream flows around said extractor during use of said extraction device; wherein when said extractor rotates during use of said extraction device said extractor creates a swirling flow pattern in said gaseous stream as said gaseous stream flows around said extractor; and wherein said swirling flow pattern increases a rate at which said liquid particulates are extracted from said gaseous stream by said upstream surface of said extractor, and also increases a rate at which said liquid particulates are extracted from said gaseous stream by said inner surface of said extraction duct.

16. The extraction device of claim 1, wherein said extraction device further comprises a source duct that has a source duct outlet; wherein said source duct outlet has a cross sectional size; wherein said source duct outlet is in fluid communication with said extraction duct; wherein said extraction duct has a cross sectional size; and wherein said cross sectional size of said extraction duct near said source duct outlet is larger than said cross sectional size of said source duct outlet.

17. The extraction device of claim 16, wherein said extractor is located near said source duct outlet.

18. The extraction device of claim 1, wherein said extraction duct further comprises an extraction duct outlet; wherein said extraction duct outlet has a cross sectional size; wherein said extraction duct has a cross sectional size; and wherein said cross sectional size of said extraction duct outlet is smaller than said cross sectional size of said extraction duct near said extraction duct outlet.

19. The extraction device of claim 18, wherein said extractor is located near said extraction duct outlet.

20. The extraction device of claim 19, wherein said exterior surface of said extractor further comprises a downstream surface; wherein said extractor further comprises a vane that is carried by said downstream surface of said extractor; wherein said extraction duct further comprises an extraction duct surface that at least partially surrounds said extraction duct outlet; wherein said vane has a downstream edge; wherein at least part of said downstream edge of said vane overlaps at least part of said extraction duct surface; and wherein at least part of said downstream edge of said vane is located near said extraction duct surface.

21. An extraction device for extracting entrained liquid particulates from a gaseous stream, wherein said extraction device comprises:
an extractor; wherein said extractor comprises an exterior surface; wherein said exterior surface comprises an upstream surface, and wherein said upstream surface comprises a periphery;
an extraction duct; wherein said extraction duct comprises an inner surface and an extracted liquid outlet, and wherein said gaseous stream passes through said extraction duct; and
an extractor mount that mounts said extractor for rotation; wherein said extractor mount mounts said extractor at least partially within said extraction duct, and within said gaseous stream;
wherein, during use of said extraction device, said extractor rotates, and at least some of said liquid particulates in said gaseous stream are extracted from said gaseous stream by said upstream surface of said extractor and form a thin film of extracted liquid on said upstream surface; wherein as said extractor rotates it creates a centrifugal force that urges said extracted liquid on said upstream surface to travel to said periphery of said upstream surface and to be flung from said periphery to said inner surface of said extraction duct; and wherein at least some of said extracted liquid on said inner surface of said extraction duct travels to said extracted liquid outlet;

wherein said extraction duct further comprises an extraction duct outlet; wherein said extraction duct outlet has a cross sectional size; wherein said extraction duct has a cross sectional size; and wherein said cross sectional size of said extraction duct outlet is smaller than said cross sectional size of said extraction duct near said extraction duct outlet;

wherein said extractor is located near said extraction duct outlet;

wherein said exterior surface of said extractor further comprises a downstream surface;

wherein said extractor further comprises a vane that is carried by said downstream surface of said extractor; wherein said extraction duct further comprises an extraction duct surface that at least partially surrounds said extraction duct outlet; wherein said vane has a downstream edge; wherein at least part of said downstream edge of said vane overlaps at least part of said extraction duct surface; and wherein at least part of said downstream edge of said vane is located near said extraction duct surface; and wherein said extractor further comprises a thin annular plate carried by at least part of said downstream edge of said vane.

22. The extraction device of claim 21, wherein said annular plate has a radial width; wherein said part of said downstream edge of said vane that overlaps at least part of said extraction duct surface has a radial width; and wherein said radial width of said annular plate is at least about equal to said radial width of said part of said downstream edge of said vane that overlaps at least part of said extraction duct surface.

23. The extraction device of claim 22, wherein said annular plate has a downstream surface; and wherein said downstream surface of said annular plate is located near said extraction duct surface.

* * * * *